US009751931B2

(12) United States Patent
Major et al.

(10) Patent No.: US 9,751,931 B2
(45) Date of Patent: Sep. 5, 2017

(54) HEPATITIS C VIRUS NEUTRALIZING ANTIBODIES AND METHODS

(71) Applicants: The United States of America, as represented by the Secretary, Department of Health and Human Services, Washington, DC (US); Federal Budgetary Research Institution State Research Center of Virology and Biotechnology "Vector", Novosibirsk (RU)

(72) Inventors: Marian Elaine Major, Alexandria, VA (US); Alla Kachko, Silver Spring, MD (US); Galina Vadimovna Kochneva, Novosibirsk (RU)

(73) Assignees: The United States of America, as represented by the Secretary, Department of Health and Human Services, Washington, DC (US); Federal Budgetary Research Institution State Research Center of Virology and Biotechnology "Vector", Novosibirsk (RU)

( * ) Notice: Subject to any disclaimer, the term of this patent is extended or adjusted under 35 U.S.C. 154(b) by 0 days.

(21) Appl. No.: 14/437,593

(22) PCT Filed: Oct. 26, 2012

(86) PCT No.: PCT/US2012/062197
§ 371 (c)(1),
(2) Date: Apr. 22, 2015

(87) PCT Pub. No.: WO2014/065822
PCT Pub. Date: May 1, 2014

(65) Prior Publication Data
US 2015/0291684 A1    Oct. 15, 2015

(51) Int. Cl.
| | | |
|---|---|---|
| C07K 16/10 | (2006.01) |
| A61K 39/29 | (2006.01) |
| A61K 45/06 | (2006.01) |
| C07K 14/005 | (2006.01) |
| C12N 7/00 | (2006.01) |
| G01N 33/576 | (2006.01) |
| C12Q 1/04 | (2006.01) |
| A61K 39/00 | (2006.01) |

(52) U.S. Cl.
CPC ............ *C07K 16/109* (2013.01); *A61K 39/29* (2013.01); *A61K 45/06* (2013.01); *C07K 14/005* (2013.01); *C12N 7/00* (2013.01); *G01N 33/5767* (2013.01); *A61K 2039/5256* (2013.01); *C07K 2317/21* (2013.01); *C07K 2317/24* (2013.01); *C07K 2317/33* (2013.01); *C07K 2317/34* (2013.01); *C07K 2317/565* (2013.01); *C07K 2317/76* (2013.01); *C07K 2317/92* (2013.01); *C12N 2770/24222* (2013.01); *C12N 2770/24234* (2013.01); *C12Q 1/04* (2013.01)

(58) Field of Classification Search
None
See application file for complete search history.

(56) References Cited

FOREIGN PATENT DOCUMENTS

| WO | 9950301 A2 | 10/1999 |
|---|---|---|
| WO | 2004087760 A1 | 10/2004 |
| WO | 2009021063 A2 | 2/2009 |

OTHER PUBLICATIONS

Kachko et al., Vaccine, 2011, 30:69-77.*
International Search Report for International Application No. PCT/US2012/062197, International filed Oct. 26, 2012, Date of mailing Aug. 5, 2013, 9 pages.
Kachko A et al.; "New Neutralizing antibody epitopes in hepatitis C virus envelope glycoproteins are revealed by dissecting peptide recognition profiles"; Vaccine; 2011; 30: 69-77; epublished Oct. 29, 2011.
Krey T et al.; "The Disulfide Bonds in Glycoprotein E2 of Hepatitis C Virus Reveal the Tertiary Organization of the Molecule"; PLOS Pathogens, vol. 6, No. 2; Feb. 2010; pp. 1-11.
Puig M et al.; "Immunization of chimpanzees with an envelope protein-based vaccine enhances specific humoral and cellular immune responses thay delay hepatitis C virus infection"; Vaccine; 2004; pp. 22: 991-1000.
Written Opinion for International Application No. PCT/US2012/062197, International filed Oct. 26, 2012, Date of mailing Aug. 5, 2013, 12 pages.

* cited by examiner

*Primary Examiner* — Nicole Kinsey White
(74) *Attorney, Agent, or Firm* — Klarquist Sparkman, LLP

(57) ABSTRACT

Novel epitope regions on hepatitis C virus E1E2 glycoprotein that induce a neutralizing antibody response in vivo are identified. Cross-neutralizing monoclonal antibodies that bind specifically to the epitopes are disclosed.

13 Claims, 9 Drawing Sheets

B: SIN-AB

HEPATITIS C VIRUS NEUTRALIZING ANTIBODIES AND METHODS

STATEMENT OF GOVERNMENT SUPPORT

This invention was made in part with government support from the United States Food and Drug Administration. The government has certain rights in this invention.

CROSS REFERENCE TO RELATED APPLICATIONS

This application is the U.S. National Stage application of PCT/US2012/062197, filed Oct. 26, 2012, the disclosure of which is incorporated herein by reference.

SEQUENCE LISTING

This application includes a sequence listing, incorporated herein by-reference in its entirety, submitted electronically with the application via EFS-WEB as an ASCII text file of 37 kB named 7DR8758.TXT and originally created Oct. 26, 2012.

BACKGROUND

Hepatitis C is an infectious disease affecting primarily the liver, caused by the hepatitis C virus (HCV). Persistent infections caused by HCV occur in 70-80% of acutely infected individuals, the majority of which will develop chronic hepatitis and will be at risk for cirrhosis, end-stage liver disease and/or hepatocellular carcinoma. Liver damage from chronic hepatitis C virus infection is now the most common cause of liver transplantation in the US.

HCV infection is treated with antiviral medications, e.g. pegylated interferon administered alone or in combination with ribavirin. Combination therapy with pegylated interferon and ribavirin is now successful in about half of the cases, but it is currently prohibitively expensive, requires long-term treatment, and is associated with serious side effects. In much of the world, such treatments are not economically feasible. New direct-acting antiviral drugs such as protease and polymerase inhibitors, either with or without interferon and/or ribavirin, have the potential to increase the response rate and to decrease the duration of treatment. However, these drugs may also have significant side effects and are extremely expensive. Two protease inhibitors are now approved in the United States for use in combination with interferon and ribavirin although the treatment costs are between $26,000-$49,000 per patient depending on the treatment duration, in addition to the costs for pegylated interferon and ribavirin (Tungol, A. et al., J Manag Care Pharm (2011) 17:685-94).

At present, there are about 17,000 new HCV infections each year in the U.S., making the development of a vaccine against this virus imperative.

The natural variability of HCV, resulting in the coexistence of quasispecies in infected individuals, could be important in hepatitis C pathogenesis. It has been postulated that immune pressure on these variants brings about the selection of escape mutants able to overcome host immune responses and establish persistent infection. The greatest genetic variability is observed in the E1 and E2 glycoproteins, posing problems for vaccine development and providing potential for escape from vaccine-induced immune responses.

The role of neutralizing antibody (nAb) in controlling viral replication during primary or secondary HCV infections is still unclear. High titers are not produced until the chronic phase of the infection. Although induction of nAbs has been associated with clearance of HCV, such antibodies may not be an absolute requirement. However, antibodies to HCV surface proteins can neutralize virus in vitro and chimpanzee vaccine studies using recombinant envelope glycoproteins (rE1E2) have shown modified infections and increased rates of clearance. Monoclonal antibodies (mAbs) have been identified that are capable of cross-neutralizing a number of different genotypes (GTs) in vitro, however, the challenge of how to induce such antibodies efficiently by vaccination, for example with recombinant antigens, still remains. Often peptide vaccination does not induce antibodies with the desired immunogenic effects and there exists very little information on antibody profiles induced by immunization with recombinant antigens or the titers of antibodies to specific neutralization epitopes.

Further, a major challenge facing HCV infected patients that undergo liver transplants is recurrence of hepatitis C virus infection following otherwise technically successful liver transplantation. Recurrent HCV infection leads to diminished graft and patient survival. Although a number of predictors of severe recurrence have been identified, no definitive strategy has been developed to prevent recurrence. Although hepatitis B virus (HBV)-specific antibody products exist that are effective in preventing recurrence of HBV infection in liver transplant patients, no HCV-specific vaccine or prophylactic treatment is available yet for preventing recurrence of HCV infection in liver transplant patients.

There remains a need in the art for more treatments of and vaccines to prevent HCV infection.

SUMMARY

Epitopes in hepatitis C virus E1 or E2 glycoprotein that induce a neutralizing antibody response in vivo and compositions comprising the epitopes are disclosed herein. Antibodies that bind specifically to an epitope and methods of making and using the antibodies and compositions are also disclosed.

Disclosed herein is an isolated antibody, which binds specifically to an epitope of hepatitis C virus (HCV).

In an embodiment, the epitope is contained within amino acid residues 264-318, 448-483, or 496-515 of the HCV polyprotein set forth in SEQ ID NO:1; or of amino acid residues 264-318, 448-483, or 496-515 of SEQ ID NO:1 with a substitution, deletion, or insertion of up to three amino acids therein.

In an embodiment, the isolated antibody is a monoclonal antibody produced from hybridoma cell 12.12 or 18.10.

Disclosed herein is a composition.

In an embodiment, the composition comprises the isolated antibody, which binds specifically to an epitope of hepatitis C virus (HCV).

In an embodiment, the composition comprises an isolated chimeric polypeptide comprising the epitope of HCV, wherein the epitope is contained within amino acid residues 264-318, 448-483, or 496-515 of SEQ ID NO:1; or amino acid residues 264-318, 448-483, or 496-515 of SEQ ID NO:1 with a substitution, deletion, or insertion of up to three amino acids therein.

Disclosed herein is a method of inducing neutralizing hepatitis C virus antibodies.

In an embodiment, the method comprises administering to a subject an isolated chimeric polypeptide comprising an epitope of Hepatitis C Virus (HCV), wherein the epitope is contained within amino acid residues 264-318, 448-483, or 496-515 of SEQ ID NO:1, or amino acid residues 264-318, 448-483, or 496-515 of SEQ ID NO:1 with a substitution, deletion, or insertion of up to three amino acids therein.

In an embodiment, the method comprises administering to a subject an isolated polynucleotide encoding an epitope of Hepatitis C Virus (HCV), wherein the epitope is contained within amino acid residues 264-318, 448-483, or 496-515 of SEQ ID NO:1, or amino acid residues 264-318, 448-483, or 496-515 of SEQ ID NO:1 with a substitution, deletion, or insertion of up to three amino acids therein.

Kits, recombinant polynucleotides, vectors, and host cells are disclosed.

Methods for detecting HCV and methods for treatment of or prophylaxis against HCV using the antibodies, polypeptides, polynucleotides, and compositions are also disclosed.

These and other advantages, as well as additional inventive features, will be apparent from the following Drawings, Detailed Description, Examples, and Claims.

BRIEF DESCRIPTION OF THE DRAWINGS

FIG. 2 presents graphs of ID50 titers of mouse sera following blocking with specific and control peptides. (A) VV-AB, (B) SIN-AB, (C) SIN-AB and VV-AB blocked with peptides representing aa264-283, 272-291, 280-318, and 496-515 combined. Error bars represent standard error of the mean of replicates within one experiment. NMS represents normal mouse serum and Flu peptide is a negative control. Experiments were performed at least 3 times with similar results.

FIG. 9 presents data showing binding in ELISA of monoclonal antibodies 12.12 and 18.10 to linear peptide representing aa496-515 of HCV genotype 1a.

FIG. 13 is a histogram showing binding of monoclonal 12.12 to Linear Peptides representing aa496-515 from other genotypes of HCV.

FIG. 14 presents two histograms showing results of an ELISA assay (left panel) and the ID50 neutralization titer (right panel) for sera obtained from various mice immunized with the cyclic 496-515 epitope peptide.

FIG. 15 presents histograms showing effect of increasing copies of the epitope in immunization on antibody induction (left) and neutralizing antibody induction (right).

DETAILED DESCRIPTION

Figure 1:
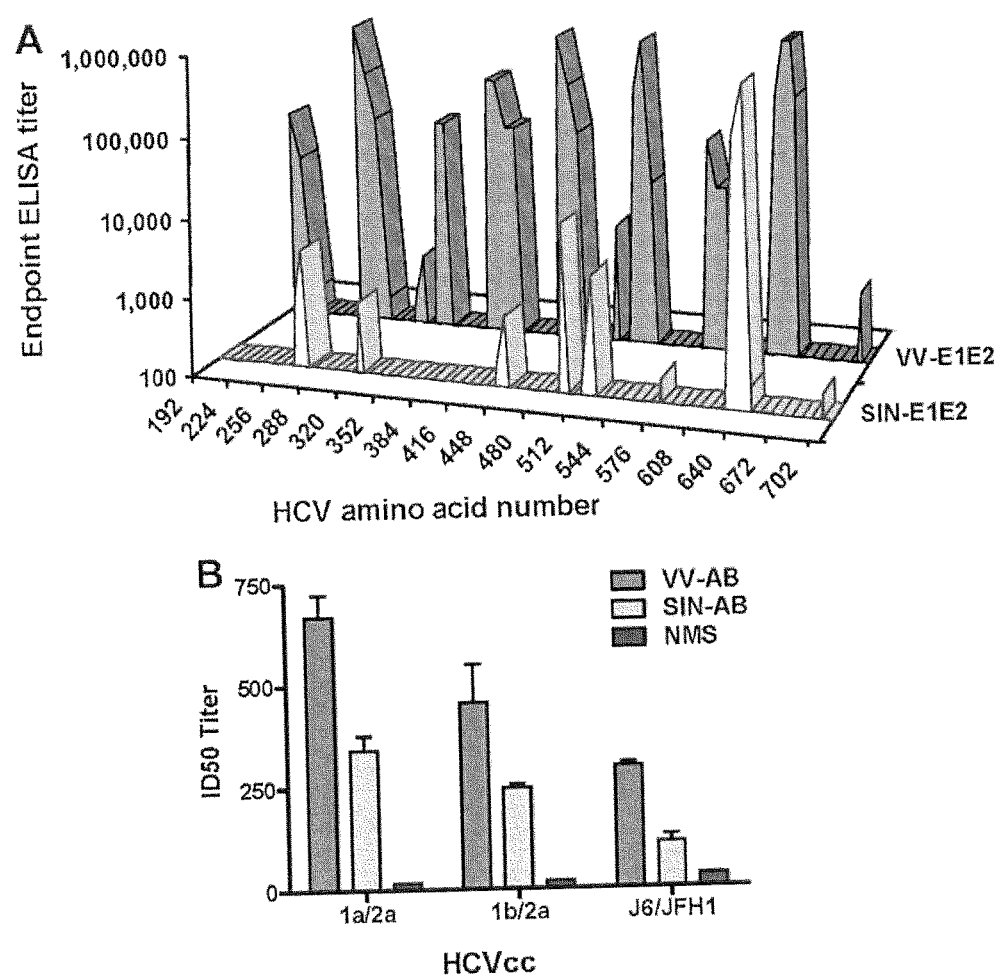
FIG. 1 presents graphs of pepscan and neutralizing antibody analysis of mouse sera. (A) Pepscan analysis of VV-E1E2- and SIN-E1E2-induced antibodies in mice. End-point titrations were determined on sera starting at 1:200 dilution. End-point titers at each dilution were calculated as the mean optical density (OD) for normal mouse serum (NMS)+4 standard deviations. (B) Neutralization of 1a/2a, 1b/2a, and J6/JFH1 cell cultured HCV (HCVcc) by VV-AB, SIN-AB and normal mouse serum (NMS). Neutralization is expressed as ID50 titer, which is the titer calculated to give 50% inhibition of the virus in cell culture. Error bars represent standard error of the mean of replicates within one experiment. Neutralization of HCVcc was performed at least 3 times with similar results.

Novel HCV E1E2 protein epitopes that induce HCV neutralizing antibodies are disclosed. In particular, one of the E2 epitopes described herein has a sequence that is highly conserved across HCV genotypes (GTs) 1-6 and antibodies induced by the conserved E2 epitope include HCV cross-neutralizing antibodies that can neutralize infectivity of multiple HCV genotypes, rather than only one or two genotypes, in vivo. Chimeric polypeptides comprising the novel epitopes are provided that induce HCV neutralizing antibodies in vivo. Unexpectedly, although chimeric polypeptides comprising the conserved E2 neutralization epitope efficiently induced antibody to the epitope in vivo in several mammals, antibody is poorly induced during natural HCV infection in human patients and chimpanzees (7 out of 68 samples positive, 10.3%) suggesting that the conserved E2 epitope is poorly presented to the immune system in the context of the viral particle. Novel monoclonal antibodies that bind to the epitopes and inhibit HCV infection of cells are also provided herein. The chimeric polypeptides and antibodies disclosed herein are useful for treatment of or prophylaxis against HCV infection.

HCV is a positive-sense RNA virus belonging to the Flaviviridae family. It encodes a single polyprotein of about 3,000 amino acids (aa). Through the action of a combination of host and viral proteases, the polyprotein is cleaved into structural proteins (core, E1, E2, and p7) and nonstructural proteins (N52-NS5B). The two envelope glycoproteins, E1 and E2, are believed to form heterodimers/oligomers on the surface of HCV particles that participate in the process of cell entry (Bartosch, B. et al., J Exp Med (2003) 197:633-642).

There are at least six known genotypes and more than 50 subtypes of HCV. The complete genotypes of many of these strains are known. See, e.g., Simmonds et al. 2005 Hepatology 42:962-973. Knowing the HCV genotype present in a subject can help predict the likelihood of the subject's treatment response and, in many cases, determine the duration of treatment.

The amino acid sequence of the full-length HCV polyprotein of genotype 1a virus H77 is presented in SEQ ID NO:1.

Three new HCV epitope regions important for neutralization of HCV were identified: amino acid (aa) residues 264-318, 448-483, and 496-515 of SEQ ID NO:1. Two of these epitope regions (designated "aa264-318" or "aa448-483") induced neutralizing antibodies that were HCV type specific. Epitope region aa496-515 of SEQ ID NO:1 (designated "aa496-515") is 85-95% conserved between HCV genotypes (GTs), and was found to induce cross-neutralizing antibodies.

A composition comprising an isolated chimeric polypeptide comprising the HCV epitope is disclosed. The epitope can be contained within amino acid residues 264-318, 448-483, or 496-515 of the HCV polyprotein set forth in SEQ ID NO:1 or of amino acid residues 264-318, 448-483, or 496-515 of SEQ ID NO:1 with substitution, deletion, or insertion of up to three amino acids therein. In some embodiments, the epitope can have a sequence of at least four contiguous amino acid residues of amino acid residues 264-318, 448-483, or 496-515 of SEQ ID NO:1 or of amino acid residues 264-318, 448-483, or 496-515 of SEQ ID NO:1 with substitution, deletion, or insertion of up to three amino acids therein. In an embodiment, the epitope is at least four contiguous amino acid residues of amino acid residues 496-515 of SEQ ID NO:1 or amino acid residues 496-515 of SEQ ID NO:1 with a substitution, deletion, or insertion of up to three amino acids therein. The isolated chimeric polypeptide can be a linear amino acid sequence or can be cyclized, reversibly or irreversibly. In an embodiment, the epitope is at least amino acid residues 504-507 or residues 503-508 of SEQ ID NO:1. The isolated chimeric polypeptide can include multiple epitopes and/or can include more than one copy of a given epitope sequence. In an embodiment, the isolated chimeric polypeptide has a sequence of amino acid residues 171-715 of SEQ ID NO:1. In an embodiment, the isolated chimeric polypeptide comprises one copy or four copies of the HCV epitope.

In another aspect, compositions comprising a nucleic acid encoding an isolated HCV epitope or an isolated chimeric polypeptide comprising the HCV epitope are disclosed. The nucleic acid sequence can be codon-optimized for expression of the HCV epitope or chimeric polypeptide in humans.

The composition can further comprise a detectable label, a solid support, an adjuvant, a pharmaceutically acceptable carrier, or a carrier molecule.

The compositions are useful as vaccines against HCV infection or as therapeutics to treat HCV infections. The compositions can also be used to detect the presence or absence of antibodies to the HCV epitopes in a biological sample.

The compositions can also be used in a method of inducing neutralizing hepatitis C virus antibodies in vivo. In an embodiment, the method comprises administering to a subject an isolated chimeric polypeptide comprising an epitope of Hepatitis C Virus (HCV), wherein the epitope is contained within amino acid residues 264-318, 448-483, or 496-515 of SEQ ID NO:1, or amino acid residues 264-318, 448-483, or 496-515 of SEQ ID NO:1 with a substitution, deletion, or insertion of up to three amino acids therein. In an embodiment, the method comprises administering to a subject an isolated polynucleotide encoding the epitope of Hepatitis C Virus (HCV).

The term "vaccine" as used herein is an antigenic preparation used to establish immunity to a disease or illness and thereby protect or cure the body from a specific disease or illness. Vaccines are either prophylactic and prevent disease or therapeutic and treat disease. Vaccines may contain more than one type of antigen. The term "vaccination" refers to the introduction of a vaccine into the body of a subject for the purpose of inducing immunity.

The term "epitope" refers to a site on an antigen that elicits an immunological response in the subject to which it is administered and to which an immunoglobulin or antibody specifically binds. Often, an epitope will bind to an antibody generated in response to such sequence. Epitopes can be formed both from contiguous amino acids or non-contiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids, and not more than about 500 amino acids (or any integer therebetween), often contiguous amino acids, in a unique spatial conformation. There is no critical upper limit to the length of the fragment, which may comprise nearly the full-length of a protein sequence, or even a chimeric protein comprising two or more epitopes from the HCV polyprotein. An epitope herein is not limited to a polypeptide having the exact sequence of the portion of the parent protein from which it is derived. Indeed, viral genomes are in a state of constant flux and contain several variable domains that exhibit relatively high degrees of variability between isolates. Thus the term "epitope" encompasses sequences identical to the native sequence, as well as modifications to the native sequence, such as deletions, additions and substitutions (generally conservative in nature) that specifically bind an antibody that specifically binds the native sequence.

The term "epitope region" denotes a linear amino acid sequence containing an epitope within the primary sequence or the tertiary folded structure of the primary sequence.

Methods for determining what epitopes are bound by a given antibody (i.e., epitope mapping) are well known in the art and include, for example, immunoblotting and immunoprecipitation assays, wherein overlapping or contiguous peptides from the antigen are tested for reactivity with the given antibody.

Methods of determining spatial conformation of epitopes are also well known in the art and include, for example, x-ray crystallography and 2- or more dimensional nuclear magnetic resonance.

An "antigen" is an entity (e.g., a proteinaceous entity or peptide) to which an antibody binds. In various embodiments disclosed herein, an antigen is a peptide derived from the HCV polyprotein comprising an epitope of E1 or E2. For example, the antigen can be HCV E1 or E2 protein or a peptide comprising aa264-318, aa448-483, and/or aa496-515 of SEQ ID NO:1.

A "detectable label" means a substance that is detectable in an assay. Examples of a detectable label include a radioactive label, an enzymatic label, a fluorescent label, a chemiluminescent label, or a dye molecule.

The term "solid support" means a material or group of materials having a rigid or semi-rigid surface or surfaces. Examples of such materials include plastics (e.g., polycarbonate or polyvinyl chloride, e.g., in sheets or microtiter wells), polyvinylidine fluoride (e.g., IMMULON®), complex carbohydrates (e.g., agarose and sepharose), acrylic resins (e.g., polyacrylamide and latex beads), nitrocellulose (e.g., in membrane or microtiter well form), glass, silicon wafers, and positively charged nylon. In some aspects, at least one surface of the solid support will be substantially flat, while in certain aspects, the solid support(s) will take the form of beads, resins, gels, microspheres, or other geometric configurations.

The term "adjuvant" means a pharmacological or immunological agent that modifies the effect of other agents, such as a drug or vaccine. They are often included in vaccines to enhance the recipient's immune response to a supplied antigen, while keeping the injected foreign material to a minimum. Examples of adjuvants include alum, $AlPO_4$, aluminum hydroxide, alhydrogel, and Lipid-A and derivatives or variants thereof, Freund's incomplete adjuvant, Freund's complete adjuvant, liposomes, non-ionic block copolymers, and MF59C.1. MF59C.1 is a submicron oil-in-water emulsion, comprising squalene, sorbitan trioleate, and polysorbate80.

A "carrier molecule" is a molecule that does not itself induce the production of antibodies harmful to the subject receiving the composition. Suitable carrier molecules are typically large, slowly metabolized macromolecules such as proteins, polysaccharides, polylactic acids, polyethylene glycol (PEG), polyglycolic acids, polymeric amino acids, amino acid copolymers, lipid aggregates (such as oil droplets or liposomes), and inactive virus particles. Such carriers are well known to those of ordinary skill in the art. The carrier molecule can be covalently or noncovalently associated with the polypeptide or nucleic acid.

The term "polypeptide" or "peptide" refers to a molecule formed from the linking, in a defined order, of at least two amino acids. The link between one amino acid residue and the next is an amide bond and is sometimes referred to as a peptide bond. A polypeptide can be obtained by a suitable method known in the art, including isolation from natural sources, expression in a recombinant expression system, chemical synthesis, or enzymatic synthesis.

The term "chimeric polypeptide" refers to a molecule, which does not occur in isolated form in nature, in which the HCV epitope is part of a linear polypeptide or a branched peptide structure. A chimeric polypeptide can include multiple copies of identical epitope sequences or can include at least one copy of multiple different epitope sequences. A branched peptide structure can have at least 2, 3, 4, 6, 8, 16, 32, 64, or more branches. The branched peptide structure can be, for example, a "multiple antigen peptide" (MAP) system. A MAP system is based on a small immunologically inert core molecule of radially branching dendrites, for example lysine dendrites, onto which a number of peptide antigens are linked, resulting in a large macromolecule having a high molar ratio of peptide antigen to core molecule which does not require further conjugation to a carrier protein. The HCV epitopes in the chimeric polypeptide may be connected directly to each other by peptide bonds or be separated by intervening amino acid sequences or non-peptide linkers via covalent linkages. The chimeric polypeptides may also contain amino acid sequences exogenous to HCV. The chimeric polypeptide can be made by any method known in the art. For example, the chimeric polypeptide can be made by a recombinant expression system or can be synthesized. Linear amino acid sequences of the chimeric polypeptide can be cyclized. Cyclization can be achieved by any method known in the art. For example, a cyclized peptide can be formed by a disulfide bond between two cysteines in the linear amino acid sequence.

The term "neutralizing antibody" is an antibody which, on mixture with an infectious agent, reduces the infectious titer of the infectious agent, e.g., an antibody that can prevent HCV from infecting a cell by neutralizing or inhibiting its biological effect, for example by blocking receptors on the cell or the virus. Neutralization can happen for example when antibodies bind to specific viral antigens, blocking the pathogen from entering their host cells.

The term "antibody" or "immunoglobulin," as used interchangeably herein, includes whole antibodies and any antigen binding fragment (antigen-binding portion) or single chain cognates thereof. An "antibody" comprises at least one heavy (H) chain and one light (L) chain. In naturally occurring IgGs, for example, these heavy and light chains are inter-connected by disulfide bonds and there are two paired heavy and light chains; these two are also inter-connected by disulfide bonds. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR) or Joining (J) regions (JH or JL in heavy and light chains respectively). Each VH and VL is composed of three CDRs three FRs and a J domain, arranged from amino-terminus to carboxy-terminus in the following order: FR1, CDR1, FR2, CDR2, FR3, CDR3, J. The variable regions of the heavy and light chains bind with an antigen. The constant regions of the antibodies may mediate the binding of the immunoglobulin to host tissues or factors, including various cells of the immune system (e.g., effector cells) or humoral factors such as the first component (Clq) of the classical complement system.

The term "antigen-binding portion" or "antigen-binding fragment" of an antibody, as used herein, refers to one or more fragments of an antibody that retain the ability to specifically bind to an antigen (e.g., HVC E2 protein aa496-515). It has been shown that fragments of a full-length antibody can perform the antigen-binding function of an antibody. Examples of binding fragments denoted as an antigen-binding portion or fragment of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb including VH and VL domains; (vi) a dAb fragment (Ward et al. (1989) Nature 341, 544-546), which consists of a VH domain; (vii) a dAb which consists of a VH or a VL domain; and (viii) an isolated complementarity determining region (CDR) or (ix) a combination of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions are paired to form monovalent molecules (such a single chain cognate of an immunoglobulin fragment is known as a single chain Fv (scFv). Such single chain antibodies are also encompassed within the term "antibody fragment." Antibody fragments are obtained using conventional techniques known to those with skill in the art, and the fragments are screened for utility in the same general manner as are intact antibodies. Antigen-binding fragments can be produced by recombinant DNA techniques, or by enzymatic or chemical cleavage of intact immunoglobulins.

The term "monoclonal antibody" means an antibody obtained from a population of substantially homogeneous antibodies, i.e., the individual antibodies comprising the population are identical except for possible naturally occurring mutations that may be present in minor amounts. In some embodiments, the term "monoclonal antibody" refers to an antibody derived from a single cell clone. Antigen binding fragments (including scFvs) of such immunoglobulins are also encompassed by the term "monoclonal antibody" as used herein. Monoclonal antibodies are highly specific, being directed against a single antigenic site. Furthermore, in contrast to conventional (polyclonal) antibody preparations, which typically include different antibodies, directed against different determinants (epitopes), each monoclonal antibody is directed against a single epitope on the antigen. Monoclonal antibodies can be prepared using any art recognized technique and those described herein such as, for example, a hybridoma method, a transgenic animal, recombinant DNA methods (see, e.g., U.S. Pat. No. 4,816,567), or using phage antibody libraries using the techniques described in, for example, U.S. Pat. No. 7,388,088 and U.S. patent application Ser. No. 09/856,907 (PCT Int. Pub. No. WO 00/31246). Monoclonal antibodies include chimeric antibodies, human antibodies and humanized antibodies and may occur naturally or be produced recombinantly.

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain embodiments, however, such recombinant human antibodies can be subjected to in vitro mutagenesis and thus the amino acid sequences of the VH and VL regions of the recombinant antibodies are sequences that, while derived from and related to human germline VH and VL sequences, may not naturally exist within the human antibody germline repertoire in vivo.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The term "human antibody" includes antibodies having variable regions in which both the framework and CDR regions are derived from human germline immunoglobulin sequences as described, for example, by Kabat et al. (Kabat, et al., Sequences of proteins of Immunological Interest, Fifth Edition, U.S. Department of Health and Human Services, NIH Publication No. 91-3242 (1991)). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences.

The human antibody can have at least one or more amino acids replaced with an amino acid residue, e.g., an activity enhancing amino acid residue that is not encoded by the human germline immunoglobulin sequence. Typically, the human antibody can have up to twenty positions replaced with amino acid residues that are not part of the human germline immunoglobulin sequence. In a particular embodiment, these replacements are within the CDR regions.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, two CDRs, or three CDRs) substantially from a non-human immunoglobulin or antibody, and further includes constant regions (e.g., one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

A non-human antibody is humanized using a method known in the art. In general, a humanized antibody has at least one amino acid residue introduced from a non-human donor. The humanization of a non-human antibody may be performed by replacing CDR sequences of a human antibody with corresponding CDR sequences of a non-human species, e.g., a rodent such as a mouse, having the desired specificity and affinity. Thus, a humanized antibody is a chimeric antibody, and a region that is smaller than the variable region of a substantially intact human antibody may be replaced by the corresponding sequences from a non-human antibody. For example, a humanized antibody may be a human antibody in which some CDR residues and possibly some framework (FR) residues are replaced by residues from the analogous CDR and FR sites in antibodies of a rodent.

The terms "specific binding," "specifically binds," "selective binding," and "selectively binds" mean that an antibody exhibits appreciable affinity for a particular antigen or epitope and, generally, does not exhibit significant cross-reactivity with other antigens and epitopes. "Appreciable" binding affinity includes binding with an affinity of at least $10^6$ $M^{-1}$, specifically at least $10^7$ $M^{-1}$, more specifically at least $10^8$ $M^{-1}$, yet more specifically at least $10^9$ $M^{-1}$, or even yet more specifically at least $10^{10}$ $M^{-1}$. A binding affinity can also be indicated as a range of affinities, for example, $10^6 M^{-1}$ to $10^{10}$ $M^{-1}$, specifically $10^7$ $M^{-1}$ to $10^{10}$ $M^{-1}$, more specifically $10^8$ $M^{-1}$ to $10^{10}$ $M^{-1}$. An antibody that "does not exhibit significant crossreactivity" is one that will not appreciably bind to an undesirable entity (e.g., an undesirable proteinaceous entity). An antibody specific for a particular epitope will, for example, not significantly crossreact with other epitopes on the same protein or peptide. Specific binding can be determined according to any art-recognized means for determining such binding. In some embodiments, specific binding is determined according to Scatchard analysis and/or competitive binding assays.

The term "linked" means a linkage of two entities, for example a labeling material and an antibody, by covalent or non-covalent bonding. A linkage mediated by a linker molecule or the like is also included.

The term "toxic material" means a material that can be linked to an antibody or a fragment thereof and can exert toxic effects on a target, such as a cancer cell. For example, radioactive materials such as yttrium-90, iodine-131, etc. and cytotoxic materials such as calicheamicin are included among toxic materials.

The term "labeling material" means a material that binds to an antibody or a fragment thereof and is detectable by a physical or chemical method to permit identification of the location or quantity of the antibody or the fragment thereof. The labeling material is used to label the antibody to make detection of bound or unbound antibody easy. Suitable detectable materials include a variety of enzymes, prosthetic groups, fluorescent materials, light-emitting materials and radioactive materials. Examples of suitable enzymes include horseradish peroxidase, alkaline phosphatase, β-galactosidase or acetylcholinesterase. Examples of suitable prosthetic groups include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride, or phycoerythrin. Examples of light-emitting materials include luminol, and examples of radioactive materials include 125I, 131I, 35S, and 3H. Detection of the labeling material can be performed by any appropriate method known in the art.

The term "isolated" refers to a nucleic acid, a polypeptide, or other component that is removed from components with which it is naturally associated. The term "isolated" can refer to a polypeptide that is separate and discrete from the whole organism with which the molecule is found in nature or is present in the substantial absence of other biological macro-molecules of the same type. The term "isolated" with respect to a polynucleotide can refer to a nucleic acid molecule devoid, in whole or part, of sequences normally associated with it in nature; or a sequence, as it exists in nature, but having heterologous sequences in association therewith; or a molecule disassociated from the chromosome.

The term "isolated nucleic acid molecule" or "isolated polynucleotide" as used in reference to nucleic acids encoding antibodies or antibody fragments (e.g., VH, VL, CDR3), refers to a nucleic acid molecule in which the nucleotide sequences are free of other genomic nucleotide sequences, e.g., those encoding antibodies that bind antigens other than HCV E2 protein EPII, which other sequences may naturally flank the nucleic acid in human genomic DNA.

The term "nucleic acid" or "polynucleotide" includes DNA molecules and RNA molecules. A nucleic acid may be single-stranded or double-stranded. A polynucleotide can be obtained by a suitable method known in the art, including isolation from natural sources, chemical synthesis, or enzymatic synthesis.

An isolated polynucleotide encoding an antibody heavy chain variable region of an antibody disclosed herein is disclosed. The isolated polynucleotide can encode an antibody heavy chain variable region having the amino acid sequence of SEQ ID NO:3 or SEQ ID NO:7. The polynucleotide can comprise SEQ ID NO: 2 or SEQ ID NO:6.

An isolated polynucleotide encoding an antibody light chain variable region of an antibody disclosed herein is disclosed. The isolated polynucleotide can encode an antibody light chain variable region having the amino acid sequence of SEQ ID NO:5 or SEQ ID NO:9. The polynucleotide can comprise SEQ ID NO:4 or SEQ ID NO:8.

Also disclosed is an isolated polynucleotide encoding an epitope of hepatitis C virus disclosed herein. The encoded epitope is contained within amino acid residues 496-515, 264-318, or 448-483 of the HCV polyprotein set forth in SEQ ID NO:1, or of amino acid residues 496-515, 264-318, or 448-483 of SEQ ID NO:1 with a substitution, deletion, or insertion of up to three amino acids therein.

The term "vector" means a nucleic acid sequence to express a target gene in a host cell. Examples include a plasmid vector, a cosmid vector, a bacteriophage vector, and a viral vector. Examples of viral vectors include a bacteriophage vector, an adenovirus vector, a retrovirus vector, and an adeno-associated virus vector.

For example, the vector may be an expression vector including a membrane targeting or secretion signaling sequence or a leader sequence, in addition to an expression control element such as promoter, operator, initiation codon, termination codon, polyadenylation signal, and enhancer. The vector may be manufactured in various ways known in the art depending on the purpose. An expression vector may include a selection marker for selecting a host cell containing the vector. Further, a replicable expression vector may include an origin of replication.

The term "recombinant vector" means a vector operably linked to a heterologous nucleotide sequence for the purpose of expression, production, and isolation of the heterologous nucleotide sequence. The heterologous nucleotide sequence can be a nucleotide sequence encoding all or part of the heavy chain or the light chain of an antibody disclosed herein.

The recombinant vector may be constructed for use in prokaryotic or eukaryotic host cells. For example, when a prokaryotic cell is used as a host cell, the expression vector used generally includes a strong promoter capable of initiating transcription (for example, pLλ promoter, trp promoter, lac promoter, tac promoter, T7 promoter), a ribosome binding site for initiating translation, and a transcription/translation termination sequence. When a eukaryotic cell is used as a host cell, the vector used generally includes the origin of replication acting in the eukaryotic cell, for example fl origin of replication, SV40 origin of replication, pMB1 origin of replication, adeno origin of replication, AAV origin of replication, or BBV origin of replication, but is not limited thereto. A promoter in an expression vector for a eukaryotic host cell may be a promoter derived from the genomes of mammalian cells (for example, a metallothionein promoter) or a promoter derived from mammalian viruses (for example, an adenovirus late promoter, a vaccinia virus 7.5K promoter, a Sindbis promoter, a SV40 promoter, a cytomegalovirus promoter, and a tk promoter of HSV). A transcription termination sequence in an expression vector for a eukaryotic host cell may be, in general, a polyadenylation sequence.

The term "operably linked" refers to a nucleic acid sequence placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

A single vector can be used to simultaneously express both the heavy chain and the light chain of the antibody. Alternatively, the heavy chain and the light chain of the antibody can be expressed from two different vectors. In the latter case, the two vectors may be introduced into a single host cell by simultaneous transduction or targeted transduction.

The host cell of the vector may be any cell that can be practically utilized by the expression vector. For example, the host cell may be a higher eukaryotic cell, such as a mammalian cell, or a lower eukaryotic cell, such as a yeast cell. Further, the host cell may be a prokaryotic cell, such as a bacterial cell. A prokaryotic host cell may be a *Bacillus* genus bacterium, such as *E. coli* JM109, *E. coli* BL21, *E. coli* RR1, *E. coli* LE392, *E. coli* B, *E. coli* X 1776, *E. coli* W3110, *Bacillus subtilis*, and *Bacillus thuringiensis*; or an intestinal bacterium, such as *Salmonella typhimurium, Serratia marcescens*, and various *Pseudomonas* species. A eukaryotic host cell may be a yeast (e.g., *Saccharomyces cerevisiae*), an insect cell, a plant cell, or an animal cell, for example, mouse Sp2/0, CHO (Chinese hamster ovary) K1, CHO DG44, PER.C6, W138, BHK, COS-7, 293, HepG2, Huh7, 3T3, RIN, or a MDCK cell line.

The polynucleotide or recombinant vector including the polynucleotide may be transferred into the host cell using a method known in the art. For example, when a prokaryotic cell is used as the host cell, the transfer may be performed using a $CaCl_2$ method or an electroporation method, and when a eukaryotic cell is used as the host cell, the transfer may be performed by microinjection, calcium phosphate precipitation, electroporation, liposome-mediated transfection, or gene bombardment, but is not limited thereto.

Disclosed herein is a recombinant vector comprising a polynucleotide encoding a heavy chain variable region or a light chain variable region of an antibody disclosed herein. In an embodiment, the recombinant vector comprises a polynucleotide consisting of SEQ ID NO: 2, 4, 6, or 8. Also disclosed is a polynucleotide encoding an epitope of hepatitis C virus disclosed herein.

A suitable host cell can be transformed with at least one of the recombinant vectors or at least one polynucleotide disclosed herein, for example a polynucleotide consisting of SEQ ID NO: 2, 4, 6, or 8. The host cell can be transformed with a recombinant vector comprising a polynucleotide consisting of SEQ ID NO: 2, and further transformed by a recombinant vector comprising a polynucleotide consisting of SEQ ID NO: 4. The host cell can be transformed with a recombinant vector comprising a polynucleotide consisting of SEQ ID NO: 4, and be further transformed by a recombinant vector comprising a polynucleotide consisting of SEQ ID NO: 2. The host cell can be transformed with a recombinant vector comprising a polynucleotide consisting of SEQ ID NO: 6, and be further transformed by a recombinant vector comprising a polynucleotide consisting of SEQ ID NO: 8. The host cell can be transformed with a recombinant vector comprising a polynucleotide consisting of SEQ ID NO: 8, and be further transformed by a recombinant vector comprising a polynucleotide consisting of SEQ ID NO: 6.

A method of isolating the antibody from the host cell is also disclosed. In an embodiment the method comprises culturing the host cell and isolating from the culture an antibody binding the HCV epitope. The method can further comprise screening the antibody in a cell culture system or in vivo to determine that it is a neutralizing antibody. In an embodiment, a genotype 1a HCV or a chimeric HCV including genotype 1a E2 aa496-515 epitope can be used in the screening assay to determine if the isolated antibody reduces infectivity of the HCV.

The term "patient" includes human and other mammalian subjects that receive either prophylactic or therapeutic treatment.

The term "subject" includes any human or non-human animal. For example, the methods and compositions of the present invention can be used to treat a subject having hepatitis C. In a particular embodiment, the subject is a human. The subject can be a human liver transplant patient. The term "non-human animal" includes all vertebrates, e.g., mammals and non-mammals, such as non-human primates, sheep, dog, cow, chickens, amphibians, reptiles, etc.

The terms "treat", "treating" and "treatment" mean implementation of therapy with the intention of reduction in severity or frequency of symptoms, elimination of symptoms or their underlying cause, prevention of the occurrence of symptoms or their underlying cause, or improvement or remediation of damage.

The term "prophylactic treatment" or "prophylaxis" against means prevention of the occurrence of symptoms of HCV infection or their underlying cause.

The term "sample" refers to tissue, body fluid, or a cell from a patient or a subject. Normally, the tissue or cell will be removed from the subject, but in vivo diagnosis is also contemplated.

The HCV genome is in a state of constant flux in vivo and contains several variable domains that exhibit relatively high degrees of variability between isolates. A number of conserved and variable regions are known between these strains and, in general, the amino acid sequences of epitopes derived from these regions will have a high degree of sequence homology, e.g., amino acid sequence homology of more than 30%, specifically more than 40%, more than 60%, and even more than 80-90%, or at least 95% homology or identity, when the two sequences are aligned.

Additionally, the term "chimeric polypeptide" may encompass polypeptides, which include modifications to the native sequence of the epitope, such as internal deletions, additions, and substitutions (generally conservative in nature), such as epitopes substantially homologous to the parent sequence. These modifications may be deliberate, as through site-directed mutagenesis, or may be accidental, such as through naturally occurring mutational events. All of these modifications are encompassed in certain embodiments so long as the modified epitope polypeptides function for their intended purpose. Thus, for example, if the chimeric polypeptides are to be used in immunogenic compositions, the modifications must be such that immunological activity (i.e., the ability to elicit a humoral or cellular immune response to the polypeptide) is not lost.

"Homology" refers to the percent identity between two polynucleotide or two polypeptide moieties. Two DNA, or two polypeptide sequences are "substantially homologous" to each other when the sequences exhibit at least about 50%, specifically at least about 75%, more specifically at least about 80%-85%, at least about 90%, and most specifically at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353-358, National Biomedical Research Foundation, Washington, D.C., which adapts the local homology algorithm of Smith and Waterman 1981 Advances in Appl Math 2:482-489, for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Alternatively, nucleotide homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. Molecular Cloning: A Laboratory Manual (2d ed., Cold Spring Harbor Laboratory Press, Cold Spring Harbor, N. Y. (1989).

The term "recombinant" can be used to describe a nucleic acid molecule and refers to a polynucleotide of genomic, RNA, DNA, cDNA, viral, semisynthetic, or synthetic origin which, by virtue of its origin or manipulation is not associated with all or a portion of the polynucleotide with which it is associated in nature.

The term "recombinant" as used with respect to a protein or polypeptide can refer to a polypeptide produced by expression of a recombinant polynucleotide. In general, the gene of interest is cloned and then expressed in transformed organisms, by a method known in the art. The host organism expresses the foreign gene to produce the protein under expression conditions.

The terms "analog" and "mutein" can refer to biologically active derivatives of a reference molecule, such as HCV E2 protein or an immunogenic fragment of E2, or fragments of such derivatives that retain desired activity, such as immunoreactivity in assays described herein. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. Preferably, the analog or mutein has at least the same immunoreactivity as the native molecule. Methods for making polypeptide analogs and muteins are known in the art.

A conservative amino acid substitution in a polypeptide sequence includes the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (He, Leu, Val, Met); and Class VI (Phe, Tyr, Trp). For example, substitution of an Asp for another class III residue such as Asn, Gln, or Glu, is a conservative substitution. One of skill in the art can readily determine regions of the molecule of interest that can tolerate change by reference to Hopp/Woods and Kyte-Doolittle plots. With respect to substitutions in antibodies, methods of identifying nucleotide and amino acid conservative substitutions which do not eliminate antigen binding are well-known in the art (see, e.g., Brummell et al., Biochem. 32:1180-1187 (1993); Kobayashi et al., Protein Eng. 12(10):879-884 (1999); and Burks et al., Proc. Natl. Acad. Sci. USA 94: 412-417 (1997)).

An "immunogenic fragment" of a particular HCV protein will generally include at least about 5-10 contiguous amino acid residues of the full-length molecule, specifically at least about 15-25 contiguous amino acid residues of the full-length molecule, and most specifically at least about 20-50 or more contiguous amino acid residues of the full-length molecule, that define an epitope, or any integer between 5 amino acids and the full-length sequence, provided that the fragment in question retains the ability to elicit an immunological response as defined herein.

Monoclonal antibodies of the invention can be produced using a variety of known techniques, such as the standard somatic cell hybridization technique described by Kohler and Milstein (1975) Nature 256: 495, viral or oncogenic transformation of B lymphocytes or phage display technique using libraries of human antibody genes. In particular embodiments, the antibodies are humanized monoclonal antibodies.

Accordingly, in one embodiment, a hybridoma method is used for producing an antibody that binds an HCV epitope disclosed herein. In this method, a mouse or other appropriate host animal can be immunized with a suitable antigen in order to elicit lymphocytes that produce or are capable of producing antibodies that will specifically bind to the antigen used for immunization. In some embodiments, the antigen is HCV E2 protein aa496-515 of SEQ ID NO:1. Alternatively, lymphocytes may be immunized in vitro. Lymphocytes can then be fused with myeloma cells using a suitable fusing agent, such as polyethylene glycol, to form a hybridoma cell (Goding, Monoclonal Antibodies: Principles and Practice, pp. 59-103 (Academic Press, 1986)). Culture medium in which hybridoma cells are growing is assayed for production of monoclonal antibodies directed against the antigen. After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

As discussed further below, a hybridoma cell producing monoclonal antibody #12.12 and a hybridoma cell producing monoclonal antibody #18.10 are disclosed herein.

The binding specificity to HCV epitopes of monoclonal antibodies, or fragments thereof, prepared using any technique including those disclosed herein, can be determined by immunoprecipitation or by an in vitro binding assay, such as radioimmunoassay (RIA) or enzyme-linked immunoabsorbent assay (ELISA) The binding affinity of a monoclonal antibody or portion thereof also can be determined by the Scatchard analysis of Munson et al., Anal. Biochem., 107: 220 (1980).

In certain embodiments, an antibody binding an HCV epitope disclosed herein, e.g., an epitope contained within aa496-515 of SEQ ID NO:1, may be further altered or optimized to achieve a desired binding specificity and/or affinity using art recognized techniques, such as those described herein.

In one embodiment, partial antibody sequences derived from a given antibody may be used to produce structurally and functionally related antibodies. For example, antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L et al., Nature 332:323-327 (1998); Jones, P. et al., Nature 321:522-525 (1986); and Queen, C. et al., Proc. Natl. Acad. See. U.S.A. 86:10029-10033 (1989)). Such framework sequences can be obtained from public DNA databases that include germline antibody gene sequences.

Thus, one or more structural features of an anti-HCV E2 aa 496-515 antibody disclosed herein, such as the CDRs, can be used to create structurally related anti-HCV E2 aa 496-515 antibodies that retain at least one functional property of the antibodies of the invention, e.g., inhibiting infection of cells exposed to HCV.

Antibody heavy and light chain CDR3 domains are known to play a particularly important role in the binding specificity/affinity of an antibody for an antigen. Accordingly, in certain embodiments, antibodies are generated that include the heavy and/or light chain CDR3s of the particular antibodies described herein. The antibodies can further include the heavy and/or light chain CDR1 and/or CDR2s of the antibodies disclosed herein.

The CDR 1, 2, and/or 3 regions of the engineered antibodies described above can comprise the exact amino acid sequence(s) as those disclosed herein. However, the ordinarily skilled artisan will appreciate that some deviation from the exact CDR sequences may be possible, particularly for CDR1 and CDR2 sequences, which can tolerate more variation than CDR3 sequences without altering epitope specificity (such deviations are, e.g., conservative amino acid substitutions). Accordingly, in another embodiment, the engineered antibody may be composed of one or more CDR1s and CDR2s that are, for example, 90%, 95%, 98%, 99%, or 99.5% identical to the corresponding CDRs of an antibody named herein.

In another embodiment, one or more residues of a CDR may be altered to modify binding to achieve a more favored on-rate of binding. Using this strategy, an antibody having ultra high binding affinity of, for example, $10^{10}$ $M^{-1}$ or more, can be achieved Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

Modifications can also be made within one or more of the framework or joining regions of the heavy and/or the light chain variable regions of an antibody, so long as antigen binding affinity subsequent to these modifications is better than $10^6$ $M^{-1}$.

In another embodiment, the antibody is further modified with respect to effector function, so as to enhance the effectiveness of the antibody in treating or preventing HCV, for example. For example, cysteine residue(s) may be introduced in the Fc region, thereby allowing interchain disulfide bond formation in this region.

In another aspect, a composition, e.g., a pharmaceutical composition, is disclosed herein that contains one or a combination of monoclonal antibodies, (or antigen-binding fragments thereof). In one embodiment, the composition includes an isolated antibody that binds an HCV epitope disclosed herein, e.g., an epitope contained within HCV E2 aa496-515. In an embodiment, the composition contains an isolated antibody disclosed herein and at least one additional therapeutic agent. The therapeutic agent can be a small molecule drug, or a biological such as a hormone, a protein, or another antibody. In some embodiments, the composition further comprises a pharmaceutically acceptable carrier. A "therapeutic agent" means a substance that when administered to a patient provides any therapeutic benefit. A therapeutic benefit may be an amelioration of symptoms of HCV infection or prevention of HCV infection.

As used herein, "pharmaceutically acceptable carrier" includes any and all solvents, dispersion media, coatings, antibacterial and antifungal agents, isotonic and absorption delaying agents, and the like that are physiologically compatible. Examples of a pharmaceutically acceptable carrier include water, saline, glycerol, and ethanol. Additionally, auxiliary substances, such as wetting or emulsifying agents, pH buffering substances, and the like, may be present in such carriers. Preferably, the carrier is suitable for intravenous, intramuscular, subcutaneous, parenteral, spinal or epidermal administration (e.g., by injection or infusion). Depending on the route of administration, the active compound, i.e., antibody, may be coated in a material to protect the compound from the action of acids and other natural conditions that may inactivate the compound.

Any composition disclosed herein can be administered alone or in combination therapy, i.e., combined with other agents. For example, the combination therapy can include a composition provided herein with at least one or more additional therapeutic agents, such as an anti-viral agent described herein, or another antibody.

Compositions can be administered by a variety of methods known in the art. As will be appreciated by the skilled artisan, the route and/or mode of administration will vary depending upon the desired results. The chimeric polypeptides, nucleic acids, or antibodies can be prepared with carriers that will protect the chimeric polypeptides, nucleic acids, or antibodies against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

To administer compositions by certain routes of administration, it may be necessary to coat the constituents, e.g., antibodies, with, or co-administer the compositions with, a material to prevent its inactivation. For example, the compositions may be administered to a subject in an appropriate carrier, for example, liposomes, or a diluent. Acceptable diluents include saline and aqueous buffer solutions. Liposomes include water-in-oil-in-water CGF emulsions as well as conventional liposomes (Strejan et al. J. Neuroimmunol. 7:27 (1984)).

Acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the antibodies, use thereof in compositions provided herein is contemplated. Supplementary active constituents can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be desirable to include isotonic agents, for example, sugars, polyalcohols such as mannitol, sorbitol, or sodium chloride in the composition. Including in the composition an agent that delays absorption, for example, monostearate salts and gelatin can bring about prolonged absorption of the injectable compositions.

Sterile injectable solutions can be prepared by incorporating the monoclonal antibodies in the required amount in an appropriate solvent with one or a combination of ingredients enumerated above, as required, followed by sterilization microfiltration. Generally, dispersions are prepared by incorporating the antibodies into a sterile vehicle that contains a basic dispersion medium and the required other ingredients from those enumerated above. In the case of sterile powders for the preparation of sterile injectable solutions, methods of preparation include vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time, or the dose may be proportionally reduced or increased as indicated by the exigencies of the therapeutic situation. For example, human antibodies may be administered once or twice weekly by subcutaneous injection or once or twice monthly by subcutaneous injection.

It can be advantageous to formulate parenteral compositions in dosage unit form for ease of administration and uniformity of dosage. "Dosage unit form" means physically discrete units suited as unitary dosages for the subjects to be treated; each unit contains a predetermined quantity of antibodies calculated to produce the desired therapeutic effect in association with the required pharmaceutical carrier. The specification for the dosage unit forms provided herein are dictated by and directly dependent on (a) the unique characteristics of the antibodies and the particular therapeutic effect to be achieved, and (b) the limitations inherent in the art of compounding such antibodies for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations include those suitable for oral, nasal, topical (including buccal and sublingual), rectal, and parenteral administration. Parenteral administration is the most common route of administration for therapeutic compositions comprising antibodies. The formulations may conveniently be presented in unit dosage form and may be prepared by any methods known in the art of pharmacy. The amount of antibodies that can be combined with a carrier material to produce a single dosage form will vary depending upon the subject being treated, and the particular mode of administration. This amount of antibodies will generally be an amount sufficient to produce a therapeutic effect. Generally, out of one hundred per cent, this amount will range from about 0.001 per cent to about ninety percent of antibody by mass, specifically from about 0.005 per cent to about 70 per cent, most specifically from about 0.01 per cent to about 30 per cent.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and infrasternal injection and infusion.

Examples of suitable aqueous and nonaqueous carriers which may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Particular examples of adjuvants which are well-known in the art include, for example, inorganic adjuvants (such as aluminum salts, e.g., aluminum phosphate and aluminum hydroxide), organic adjuvants (e.g., squalene), oil-based adjuvants, virosomes (e.g., virosomes which contain a membrane-bound hemagglutinin and neuraminidase derived from the influenza virus).

Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

When compositions are administered as pharmaceuticals, to humans or animals, they can be given alone or as a pharmaceutical composition containing, for example, 0.001 to 90% (more specifically, 0.005 to 70%, such as 0.01 to 30%) of active ingredient in combination with a pharmaceutically acceptable carrier.

Regardless of the route of administration selected, compositions provided herein, may be used in a suitable hydrated form, and they may be formulated into pharmaceutically acceptable dosage forms by conventional methods known to those of skill in the art.

Actual dosage levels of the antibodies in the pharmaceutical compositions provided herein may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the composition required. For example, the physician or veterinarian could start doses of the antibodies at levels lower than that required to achieve the desired therapeutic effect and gradually increasing the dosage until the desired effect is achieved. In general, a suitable daily dose of compositions provided herein will be that amount of the antibodies which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six, or more sub-doses administered separately at appropriate intervals throughout the day, optionally, in unit dosage forms. While it is possible for antibodies to be administered alone, it may be desirable to administer antibodies as a formulation (composition).

Therapeutic compositions can be administered with medical devices known in the art. For example, in a specific embodiment, a therapeutic composition can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in methods disclosed herein include: U.S. Pat. No. 4,487,603, which discloses an implantable micro-infusion pump for dispensing medication at a controlled rate; U.S. Pat. No. 4,486,194, which discloses a therapeutic device for administering medications through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the monoclonal antibodies can be formulated to ensure proper distribution in vivo. For example, the therapeutic can be formulated in liposomes. Methods of manufacturing liposomes are known in the art. The liposomes may comprise one or more moieties that are selectively transported into specific cells or organs, thus enhance targeted drug delivery.

Also provided are methods of using antibodies (and antigen binding fragments thereof) that bind the HCV epitopes disclosed herein in a variety of ex vivo and in vivo diagnostic and therapeutic applications involving HCV.

Accordingly, in one embodiment, the antibody or a fragment thereof specifically binding an HCVepitope which is contained within aa264-318, aa448-483, or aa496-515 of SEQ ID NO:1 can be used to detect HCV in a sample. In some embodiments, the antibody or a fragment thereof specifically binding the HCV epitope can be used to detect HCV genotype 1a in a sample. In some embodiments, the antibody or a fragment thereof specifically binding an HCV epitope contained within aa496-515, e.g., aa504-507, can be used to detect any HCV genotype in a sample. In an embodiment, the method comprises contacting the antibody with a sample under conditions such that the antibody binds the HCV epitope; and detecting antibody bound to the HCV epitope. Such a method could be a component of a diagnostic method for HCV infection or for a method of identifying the genotype of HCV infection, for example to optimize treatment.

Methods for treating or prophylaxis against HCV infection by administering compositions disclosed herein to a subject are also provided.

In an embodiment, the method comprises administering a composition comprising an isolated chimeric polypeptide comprising the HCV epitope, wherein the epitope has a sequence of amino acid residues 264-318, 448-483, or 496-515 of SEQ ID NO:1 or a sequence of amino acid residues 264-318, 448-483, or 496-515 of SEQ ID NO:1 with a substitution, deletion, or insertion of up to three amino acids therein. In an embodiment, the method comprises administering a composition comprising a nucleic acid encoding the isolated HCV epitope or an isolated chimeric polypeptide comprising the HCV epitope. The epitope can be contained within amino acid residues 264-318, 448-483, or 496-515 of the HCV polyprotein set forth in SEQ ID NO:1 or of amino acid residues 264-318, 448-483, or 496-515 of SEQ ID NO:1 with substitution, deletion, or insertion of up to three amino acids therein. In an embodiment, the epitope has a sequence of at least four contiguous amino acids of amino acid residues 264-318, 448-483, or 496-515 of the HCV polyprotein set forth in SEQ ID NO:1 or of amino acid residues 264-318, 448-483, or 496-515 of SEQ ID NO:1 with substitution, deletion, or insertion of up to three amino acids therein. In an embodiment, the method for treating or preventing HCV infection comprises administering to a subject an HCV neutralizing antibody disclosed herein.

In the method, the compositions, polypeptides, nucleic acids, or HCV neutralizing antibodies can be administered alone or in combination with one or more additional therapeutic agents. Any composition disclosed herein, including a polypeptide, nucleic acid, or antibody, can be administered alone or with another therapeutic agent that acts in conjunction with or synergistically with the polypeptide, nucleic acid, or antibody to treat or provide prophylaxis against HCV infection. Such therapeutic agents include those described herein, for example, small organic molecules, monoclonal antibodies, and recombinantly engineered biologics.

In some embodiments, the subject can be a liver transplant patient, specifically the liver transplant patient can have chronic hepatitis C. A "liver transplant patient" is a patient in any stage associated with obtaining a liver transplant, including for example a patient with liver disease evaluated as needing a liver transplant, a patient scheduled for a liver transplant, or a patient post-liver transplant.

The polypeptides, nucleic acids, or HCV neutralizing antibody can be administered in an amount effective to treat or prevent HCV infection.

The term "effective amount," as used herein, refers to that amount of polypeptide, polynucleotide, or antibody, which is sufficient to effect treatment of or prevent symptoms of HCV infection when administered to a subject. The exact amount necessary will vary depending on the subject being treated; the age and general condition of the individual to be treated; the capacity of the individual's immune system to synthesize antibodies; the relative activity of the antibodies (e.g., in inhibiting HCV infection of cells); the degree of protection desired; the severity of the condition being treated; the particular macromolecule selected and its mode of administration, among other factors. An appropriate effective amount can be readily determined by one of skill in the art. A "therapeutically effective amount" will fall in a relatively broad range that can be determined through routine trials using in vitro and in vivo models known in the art.

Typically, the compositions described above are prepared as injectables, either as liquid solutions or suspensions; solid forms suitable for solution in, or suspension in, liquid vehicles prior to injection may also be prepared. Thus, once formulated, the compositions are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule. Specifically, the effective amount is sufficient to bring about treatment or prevention of disease symptoms. The exact amount necessary will vary depending on the subject being treated; the age and general condition of the individual to be treated; the capacity of the individual's immune system to synthesize antibodies; the degree of protection desired; the severity of the condition being treated; the particular macromolecule selected and its mode of administration, among other factors. An appropriate effective amount can be readily determined by one of skill in the art. A "therapeutically effective amount" will fall in a relatively broad range that can be determined through routine trials using in vitro and in vivo models known in the art.

For example, the composition can be injected intramuscularly to a large mammal, such as a primate, for example, a baboon, chimpanzee, or human. The amount of polypeptide administered will generally be about 0.1 µg to about 5.0 mg per dose, or any amount between the stated ranges, such as 0.5 µg to about 10 mg, 1 µg to about 2 mg, 2.5 µg to about 250 µg, 4 µg to about 200 µg, such as 4, 5, 6, 7, 8, 9, 10, 20, 30, 40, 50, 60, 70, 80, 90, 100 µg per dose. The compositions can be administered either to a subject, e.g., a mammal, that is not infected with an HCV or can be administered to an HCV-infected subject.

Administration of the chimeric polypeptides or polynucleotides encoding the polypeptides can elicit a cellular immune response, and/or an anti-HCV epitope antibody titer in the mammal that lasts for at least 1 week, 2 weeks, 1 month, 2 months, 3 months, 4 months, 6 months, 1 year, or longer. The polypeptides or polynucleotides encoding the polypeptides can also be administered to provide a memory response. If such a response is achieved, antibody titers may decline over time, however exposure to HCV or immunogen results in the rapid induction of antibodies, e.g., within only a few days. Optionally, antibody titers can be maintained in a mammal by providing one or more booster injections of the polypeptides at 2 weeks, 1 month, 2 months, 3 months, 4 months, 5 months, 6 months, 1 year, or more after the primary injection.

Specifically, an antibody titer of at least 10, 100, 150, 175, 200, 300, 400, 500, 750, 1,000, 1,500, 2,000, 3,000, 5,000, 10,000, 20,000, 30,000, 40,000, 50,000 (geometric mean titer), or higher, is elicited, or any number between the stated titer, as determined using a standard immunoassay, such as the immunoassay described in, e.g., Chien et al., Proc Natl Acad Sci USA 89: 10011-5 (1992).

In order to determine whether the polypeptides or polynucleotides encoding the polypeptides are capable of eliciting a neutralizing antibody reaction, neutralization assays can be performed using techniques well known in the art. For example sera can be isolated from an immunized subject and analyzed using an HCV pseudoparticle (HCVpp) assay, as described in e.g., Bartosch et al. 2003 J Exp Med 197:633-642 or using an HCV cell culture (HCVcc) system that allows a relatively efficient amplification of virus, as described in Lindenbach et al., Science 309: 623-6 (2005); and Wakita et al., Nat Med. 11: 791-6 (2005). Additionally, assays to determine the presence of neutralization of binding (NOB) antibodies can be performed as described in, e.g., Rosa et all 996 Proc Natl Acad Sci USA 93:1759.

Immune responses of the subject, e.g., a mammal, generated by the delivery of the aforementioned compositions can be enhanced by varying the dosage, route of administration, or boosting regimens. The compositions described herein may be given in a single dose schedule, or in a multiple dose schedule in which a primary course of vaccination includes 1-10 separate doses, followed by other doses given at subsequent time intervals required to maintain and/or reinforce an immune response, for example, at 1-4 months for a second dose, and if needed, a subsequent dose or doses after several months.

The dosages of polynucleotide or antibody for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an antibody or antigen binding portion thereof, according to the invention. Dosage regimens may be adjusted to provide the optimum therapeutic response. An effective amount is also one in which any toxic or detrimental effects (i.e., side effects) of an antibody or antigen binding fragment thereof are minimized and/or outweighed by the beneficial effects.

Also provided are kits comprising at least one composition, polypeptide, nucleic acid, and/or HCV neutralizing antibody disclosed herein, optionally contained in a single vial, and may include, e.g., instructions for use in treating or preventing HCV infection. The kits may include a label indicating the intended use of the contents of the kit. The term label includes any writing, marketing materials or recorded material supplied on or with the kit, or which otherwise accompanies the kit.

The kit can be a diagnostic kit for detecting an HCV-specific antigen in a sample. In an embodiment, the kit comprises at least one HCV neutralizing antibody disclosed herein and reagents for detecting a complex between the antibody and an HCV-specific antigen. For example, the kit can include a buffer that enables binding reaction between the antibody and the HCV antigen in a biological sample, or components for producing the buffer.

Other embodiments of the present invention are described in the following non-limiting Examples.

EXAMPLES

Example 1

Identification of New HCV Epitopes

In this study we compared and analyzed antibody profiles induced following immunization with HCV rE1E2 proteins produced from Vaccinia (VV) and Sindbis (SIN) virus systems. The quality of antibodies was assessed using peptide scanning and in vitro neutralization assays employing cell culture viruses (HCVcc) expressing envelope proteins from 3 different subtypes of HCV (1a (H77), 1b (LB) (GENBANK accession number HQ110091.1) and 2a (J6/JFH1)).

Using peptide blocking and antibody isolation, we found that the most immunogenic epitopes induce non-neutralizing antibodies. We identified three new regions important for neutralization. Two of these regions are type specific; antibodies to the third region, which is 85-95% conserved between genotypes (GTs), were found to be cross-neutralizing. These data are important for vaccine development and suggest that removing some immunogenic sites from proteins may improve presentation and immune responses to nAb epitopes.

Materials and Methods

Recombinant Sindbis (SIN) and Vaccinia virus (VV) rE1E2 constructs were constructed expressing aa171-715 of GT 1a HCV (H77) (SEQ ID NO:1) with a carboxy terminus 6-HIS tag, as previously described (Major M E, et al. J Virol 1999; 73(April (4)):3317-25; Puig M, et al. Vaccine 2004; 22:991-1000).

Proteins were purified by GNL lectin-affinity chromatography (Vector Labs, Burlingame, Calif.) and a His-Bind Ni2+ column (Novagen, Madison, Wis.) (Puig M, et al. Vaccine 2004; 22: 991-1000) from infected BHK cells. Specificity and purity (>80%) were determined by Western blotting, using anti-E1 (A4) and/or anti-E2 (A11) mAbs (Dubuisson J, et al. J Virol 1994; 68:6147-60), and silver staining of proteins separated on polyacrylamide gels. Peak fractions were pooled for further purification or for use in immunization.

For deglycosylation, proteins were treated with Peptide: N-glycosidase F (PNGase F) (New England Biolabs, Beverly, Mass.) according to the manufacturer's instructions.

BALB/c mice were intraperitoneally immunized with 5 μg purified rE1E2 in Freund's Complete Adjuvant (CFA) (Sigma, Mo.). Control mice were injected with PBS+CFA (normal mouse serum). After 30 and 60 days, animals received intraperitoneal booster injections: 5 μg rE1E2 in Freund's Incomplete Adjuvant (Sigma, Mo.). Final bleeds were performed 3 weeks after the final boosts.

The immunization of chimpanzees Ch1587 and Ch1601 with SIN-E1E2 has been previously described (Puig M, et al. Vaccine 2004; 22: 991-1000).

Biotinylated peptide enzyme-linked immunosorbent assays (ELISAs) were performed using biotinylated peptides (20mers overlapping by 12) covering the entire E1E2 region (Mimotopes, Victoria, Australia), as previously described (Major M E, et al. J Virol 1999; 73(April (4)): 3317-25).

Blocking antibody to specific peptides was performed as previously described (Major M E, et al. J Virol 1999; 73(April (4)):3317-25) using 1-5 μg of non-biotinylated peptides in 100 μl of serum Affinity purification was performed by incubating biotinylated peptides (1-5 μg) with serum, 60 min at room temperature (RT). Streptavidin coated magnetic beads (Dynabeads-M-280, Invitrogen, CA) were blocked with 5% milk/PBS and incubated with peptide/serum samples, 60 min RT. After washing, bound antibody was eluted with 0.2 M glycine-HCl (pH 2.2), 10 min RT, and neutralized immediately with 1 M Tris-HCl (pH 9.1).

ID50 and ID90 titers, the titers determined to neutralize 50% and 90% of the virus, respectively (Reed L. J., Muench H., Am. J Hyg. 27(3):493-7 (1938)), were calculated by performing 2-fold dilutions of sera beginning at 1:32 and ending at 1:4096 in complete DMEM. HCVcc (50 ffu/50 μl) stocks were mixed with serum and incubated at 37° C. for 1 h before infection (100 μl/well) of Huh-7.5 cells (Blight K J, et al., J. Virol. 76 (24)):13001-14 (December 2002)). Cells were cultured for 3 days then fixed and stained (Lindenbach B D, et al., Science 309(5734)):623-6 (2005)). Neutralizations were performed in duplicate; foci consisting of ≥3 cells were counted as positive. Negative controls were represented by normal mouse serum (NMS); normal human serum (Innovative Research, Novi, Mich.) and chimpanzee sera obtained prior to immunization/challenge. Titers are expressed as a reciprocal of the dilution calculated to neutralize 50% of the virus. The dilution of sera began at 1:32; if a 1:32 dilution did not reduce infectivity by 50% we assigned what would have been the next lowest dilution to the sample i.e. 1:16.

The concentration of IgG, IgA and IgM in samples was assessed using Ig ELISA kits for human sera specific for each Ig subclass (Alercheck, Mass.) according to the manufacturer's instructions. A commercially prepared 5% (50 mg/mL) immune globulin preparation was included as an internal control for IgG testing which returned a value of 45.65 mg/mL (Zhang P, et al. Proc Natl Acad Sci USA 106(18):7537-41 (May 2009))

Results 3.1. Purification of rE1E2 Proteins

The rE1E2 proteins were analyzed at each stage of the purification process by Western blot. Differences in glycosylation levels of VV and SIN-E1E2 were consistently observed before and after purification. The SIN-E1E2 proteins were incompletely glycosylated, demonstrated by a series of bands on the Western blots. This was confirmed through deglycosylation of the Sindbis E1E2 preparation using PNGase F. Following treatment single bands at 20 kDa, 36 kDa and 57 kDa were observed which correspond to the molecular weights of unglycosylated E1, E2 and E1E2, respectively. Despite the differences in glycosylation the proteins could be purified to similar levels (>80% pure) as assessed by Coomassie blue or silver staining and showed similar profiles when analyzed under nonreducing conditions. From the analysis of non-reduced proteins it appeared that there were more high molecular weight complexes in the SIN-E1E2 preparation compared to VV-E1E2, suggesting a greater proportion of aggregated complexes. Staining of the non-reduced proteins with anti-E1 antibody alone revealed E1 monomers, dimers, and aggregates. Using anti-E2 antibody alone for Western blots of non-reduced proteins revealed only high molecular weight aggregates.

3.2. Antibody Responses in Immunized Mice

Sera from the VV-E1E2 and SIN-E1E2 immunized mice were designated VV-AB and SIN-AB, respectively. Sera positive for envelope antibodies in ELISA using whole antigen were pooled and further analyzed by Pepscan ELISA, a procedure for mapping and characterizing epitopes involving the synthesis of overlapping peptides and analysis of the peptides by ELISAs.

The SIN-AB displayed a narrow recognition profile (FIG. 1A). By end-point titration we identified 4 determinants with titers>1:800 (aa264-318; aa496-515; aa512-547; and aa632-667), whereas 9 determinants were recognized by VV-AB (FIG. 1A) with end-point titers>1:50,000. Each of the 4 regions recognized by SIN-AB was also recognized by VV-AB. SIN-AB displayed a higher titer against one region, aa496-515, the respective titers for SIN-AB and VV-AB against this epitope were calculated as 1:12,800 and 1:3200.

3.3. In Vitro Neutralization of HCVcc with Mouse Sera

ID50 titers were determined for VV-AB and SIN-AB against 1a/2a, 1b/2a and 2a (J6/JFH1) HCVcc (FIG. 1B). Despite the broader peptide recognition profile and higher ELISA titers, the ID50 titer of VV-AB was only about 2.0-fold higher than SIN-AB against the 1a/2a and 1b/2a HCVcc. Both serum samples were also able to neutralize more than 90% of HCVcc 1a/2a although only at dilutions of about 1:64 and 90% neutralization was not obtained in all assays performed. For assays where 90% neutralization was obtained, the mean ID90 titers against HCVcc 1a/2a for VV-AB and SIN-AB were calculated as 67.5 and 45.9, respectively. In addition, SIN-AB was able to crossneutralize J6/JFH1 (FIG. 1B), although VV-AB showed an almost 3-fold better cross-neutralization of J6/JFH1 (ID50=295) compared to SIN-AB (ID50=109).

3.4. ID50 Titers of Blocked and Unblocked Mouse Sera

In order to assess which determinant-specific antibodies contributed to neutralization we performed blocking assays prior to neutralization and compared the ID50 titer to sera blocked with Flu peptides. ELISA signals were assessed after blocking with Flu or HCV-specific peptides covering the 4 determinants recognized by both SIN-AB and VV-AB. A number of determinants (e.g. aa264-318) were represented by more than one of the over-lapping peptides in the Pepscan therefore all peptides were used for blocking and a reduction in signal against all peptides was verified by ELISA. In all cases peptide blocking reduced the specific ELISA signal substantially.

The same serum samples were then tested in neutralization assays with 1a/2a HCVcc. Despite substantial blocking of antibodies to the 3 peptides covering the major determinant recognized by both VV-AB and SIN-AB (aa632-667), there was little effect on neutralization of 1a/2a HCVcc by either sample, FIGS. 2A and B. The ratios of mean ID50 titers for Flu-blocked sera and aa632-667-blocked sera were 1.07 and 1.2 for VV-AB and SIN-AB, respectively. A similar result was obtained using peptides encompassing aa512-547 (FIGS. 2A and B). Blocking antibodies specific to this region marginally reduced ID50 titers from 753.6 to 691.7 (ratio=1.1; 8.2% reduction) and from 545.6 to 505.2 (ratio=1.1; 7.4% reduction) for VV-AB and SIN-AB, respectively. However, blocking SIN-AB with a peptide representing aa496-515 reduced neutralization of 1 a/2a HCVcc by 72% from 545.6 to 152.6 (FIG. 2B). Blocking the same peptide-specific antibodies in VV-AB reduced neutralization but to a lesser degree, the ID50 titer decreased 34.1% from 753.6 to 495.9. This is consistent with the lower reactivity of VV-AB to this epitope and suggests antibodies to aa496-515 play a lesser role in neutralization with VV-AB where antibodies are present that recognize known neutralization epitopes, specifically E2 hypervariable region 1 (HVR1) (aa 391-410) and aa412-426, than with SIN-AB where antibodies to aa496-515 seem to represent the major neutralizing response. Blocking antibodies to aa264-318 also reduced ID50 titers for 1a/2a HCVcc by 27% and 21.7% for VV-AB and SIN-AB, respectively. These data suggested that the regions aa264-318 and aa496-515 contain neutralization epitopes. In order to assess whether antibodies to these two regions represent the majority of neutralizing activity in SIN-AB we blocked the same serum sample with peptides representing both regions. The ELISA signals were substantially reduced after blocking with the combined peptides. Blocking SIN-AB with both sets of peptides led to almost complete abrogation of neutralizing activity reducing the ID50 titer to 75.7, similar to that seen for normal mouse serum (NMS) (69.5) (FIG. 2C). However, combining the peptides to block VV-AB did not reduce the ID50 titer beyond that seen when peptides to the individual regions were used, further suggesting that these antibodies do not represent the major neutralizing activity in this preparation.

3.5. Identification of Cross-neutralizing Antibodies in Mouse Sera

VV-AB serum was shown by Pepscan to contain antibodies to a number of epitopes (FIG. 1A) including HVR1 (aa391-410) and EPI (aa412-419), a conserved epitope downstream from HVR1. Antibodies to EPI have been shown to be broadly cross-neutralizing.

Figure 2:
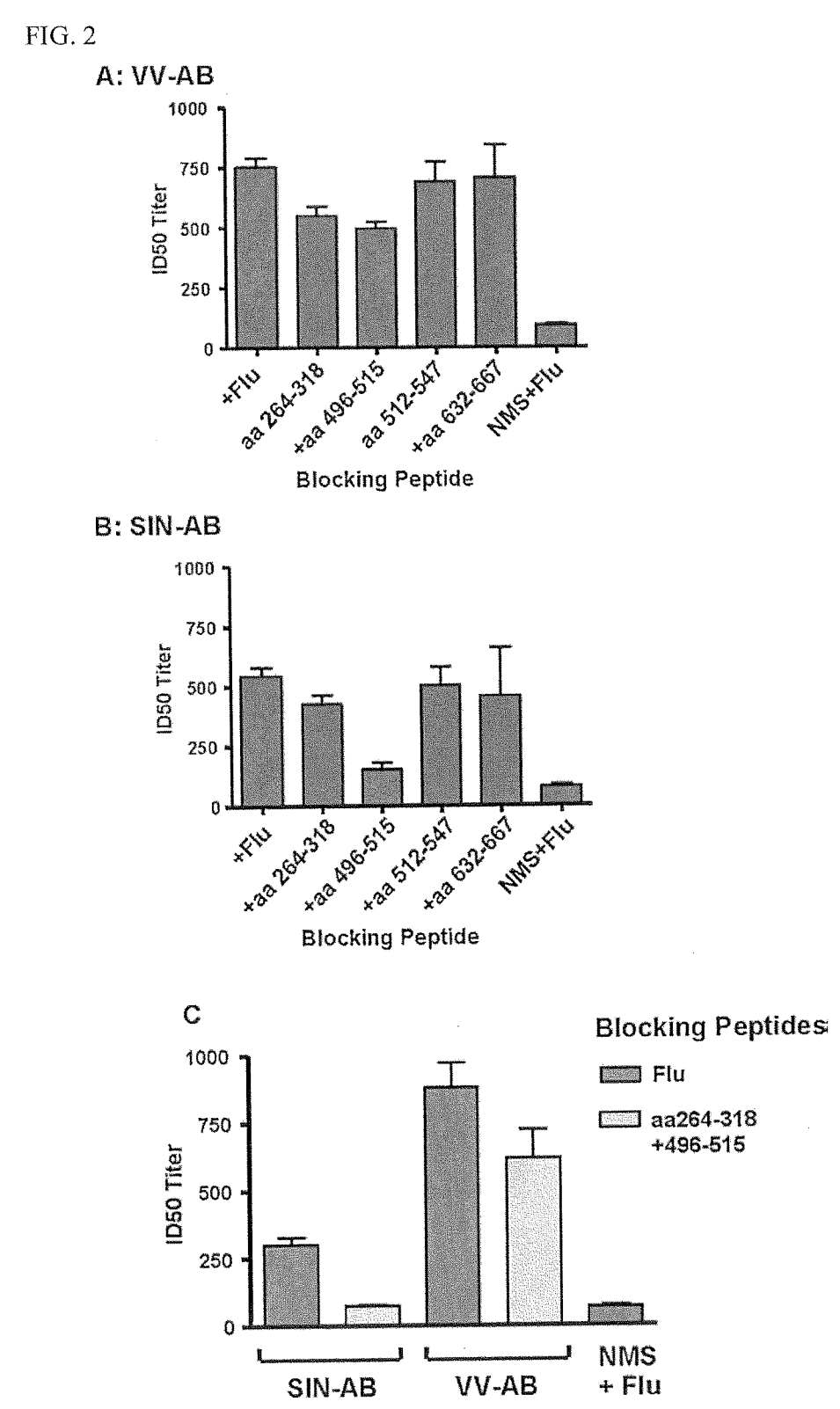
Figure 3:
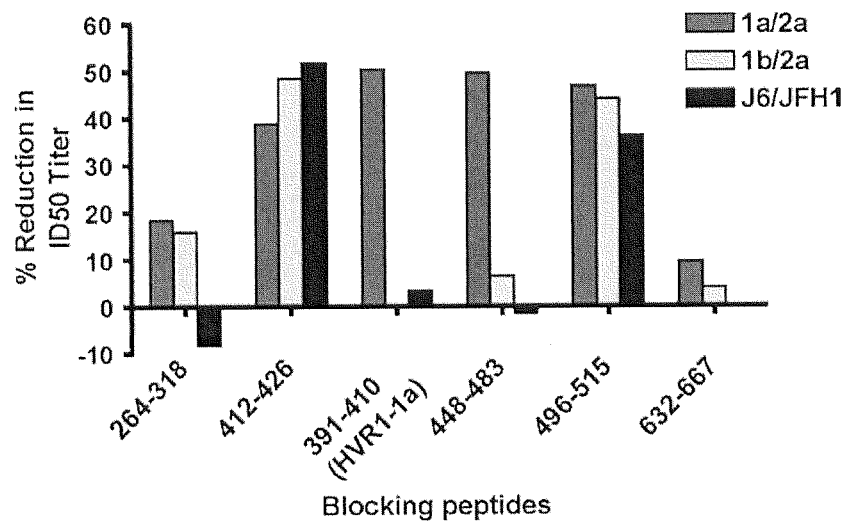
FIG. 3 is a graph of percentage reduction in ID50 titers of VV-AB following blocking with specific peptides. Cell cultured HCV (HCVcc) 1a/2a, 1b/2a and J6/JFH1 were used to test the effects of blocking. Regions blocked are shown on the X-axis. Percentage reduction was calculated as ((ID50 of Flu peptide blocked sera−ID50 HCV peptide blocked sera)/ID50 of Flu peptide blocked sera)×100.

In order to confirm that additional antibodies in the VV-AB preparation have neutralizing activity and to examine the role of antibodies to specific epitopes in cross-neutralization, we performed neutralization assays using 1a/2a, 1b/2a and J6/JFH1 HCVcc using blocked and Flu-blocked VV-AB. The results are presented in FIG. 3. ELISA signals were substantially reduced after blocking of the VV-AB. In order to ensure that carry-over peptide from the blocking experiments did not impact viral infection, we incubated virus with specific peptides at the concentrations used in the blocking assays and performed a standard infection of Huh-7.5 cells. No impact on infectivity levels was noted. The effect of specific blocking on neutralization is shown in FIG. 3 as % change in ID50 titers relative to the ID50 titer of the Flu-treated VV-AB against the same HCVcc. Blocking antibodies to aa632-667 had little effect on neutralization of the 3 viruses tested, which is consistent with the data shown in FIG. 2. In addition blocking antibodies to aa200-235, aa312-339 and aa702-721 had little effect on neutralization (data not shown). However, blocking antibodies to aa264-318 resulted in about 20% reduction in the ID50 titer to both 1a/2a and 1b/2a HCVcc but had no effect on the neutralization of J6/JFH1, suggesting the region is not conserved in this GT2a HCVcc.

The percent amino acid sequence identity of genotype 1b (LB) and 2a (J6/JFH1) sequences present in the HCVcc used in these experiments was compared to genotype 1a (H77) present in the 1a/2a HCVcc chimera for each of the amino acid regions studied. The results are shown in Table 1.

TABLE 1

Percentage identity between 1b (LB) and 2a (J6/JFH1) sequences encoded by the HCVcc used in this study compared to the H77 1a sequence encoded by the 1a/2a HCVcc chimera used in this study.

| Amino acid region | % identity | |
| --- | --- | --- |
|  | 1b | 2a |
| 264-318 | 83.3 | 63.9 |
| 412-426 | 93.3 | 86.7 |
| 391-410 (HVR1) | 36.8 | 36.8 |
| 448-483 | 66.7 | 44.4 |
| 496-515 | 90 | 85 |

Based on Table 1, there is higher conservation of the aa264-318 region in the 1b/2a HCVcc chimera (83.3%/c3.9%) than in the J6/JFH1 (GT2a) HCVcc (63.9%).

Blocking antibodies to HVR1 (aa391-410) or aa448-483 substantially reduced the neutralization of 1a/2a HCVcc but did not affect neutralization of 1b/2a or J6/JFH1. Conversely, blocking aa412-426 (EPI) reduced neutralization of 1a/2a, 1b/2a, and J6/JFH1 by up to 50%. Finally, blocking antibodies to aa496-515 affected neutralization of all 3 HCVcc. Table 1 shows that the aa496-515 region is highly conserved between each of the 3 HCVcc viruses studied. This data confirms the specificity of the blocking assays and demonstrates that the region aa496-515 represents a new, conserved neutralization epitope.

Figure 4:
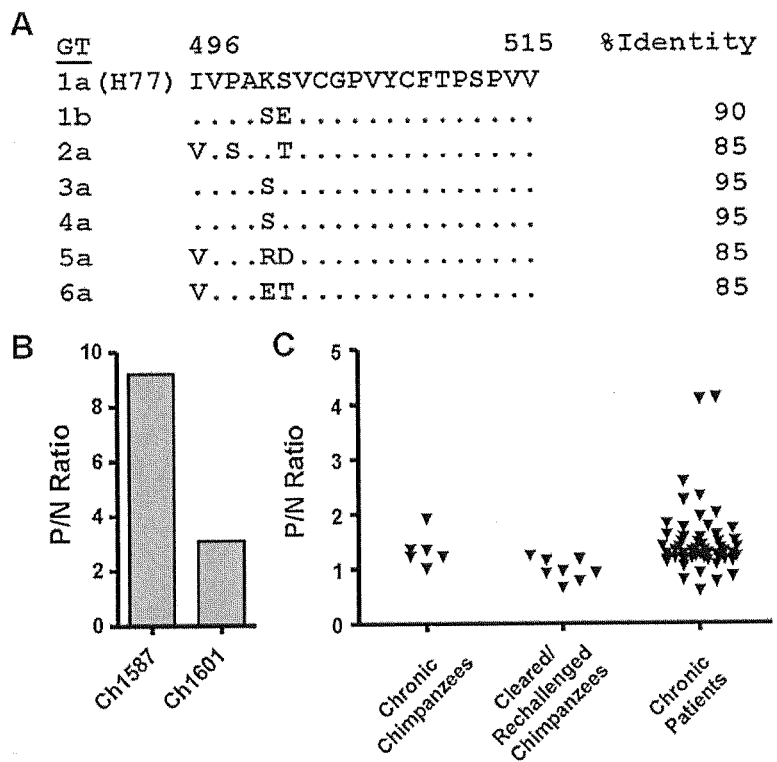
FIG. 4 shows the conservation of 496-515 sequence and reactivity of patient and chimpanzee sera. (A) Alignment of prototype sequences corresponding to aa496-515 of SEQ ID NO:1 (top sequence) from HCV genotypes 1-6 is shown. Substitutions in particular positions of aa496-515 of SEQ ID NO:1 present in GT1b, 2a, 3a, 4a, 5a, or 6a are represented in the rows below the GT 1a sequence. Sequences were obtained from the Los Alamos HCV Sequence Database (Kuiken C, et al. The Los Alamos HCV Sequence Database, Bioinformatics (2005), 21(3):379-84). (B) Reactivity of sera from vaccinated chimpanzees to peptide 496-515. Sera were diluted 1:1000. P/N ratio represents the OD of the positive sample divided by the OD of a negative serum sample from the same animal. (C) Reactivity of sera from chimpanzees and patients infected with HCV. Sera were diluted 1:100. For the chimpanzee data P/N ratio represents the OD of the positive sample divided by the OD of a negative serum sample from the same animal. For the patient samples the P/N ratio represents the OD of the test samples divided by the mean OD value of signals from negative human sera.

Conservation of aa496-515 was examined using prototype sequences from HCV genotypes (GTs) 1-6. Alignment of the sequences relative to GT1a is shown in FIG. 4A. The greatest conservation of the GT1a sequence was seen with GT1b (90%) and the greatest diversity was seen with GT2a, GT5a and GT6a (85%) (FIG. 4A). Residues 502-515 were 100% conserved between genotypes.

3.6. Induction of Antibodies to aa496-515 in Naturally Infected or Vaccinated Patients and Chimpanzees We tested reactivity of serum samples from chimpanzees (n=2) vaccinated with SIN-rE1E2 (Puig M, et al. Vaccine 2004; 22: 991-1000)); acute phase samples from chimpanzees that cleared HCV (n=5, taken at seroconversion (Major M E, et al. Hepatology 2004; 39(June (6)):1709-20)); rechallenged chimpanzees (n=3, taken 2-3 weeks after rechallenge); chronically infected chimpanzees (n=6, infected with GT1a (H77) for >3 years) and chronically infected human patients (GTs 1b; 2a; 2b; 2a/2c; and 3a viruses (n=54)).

The results, shown in FIGS. 4B and 4C, show that antibodies to epitope aa496-515 are induced effectively by vaccination with the recombinant E1E2 protein, but are poorly induced during natural infection.

The vaccinated chimpanzees developed substantial levels of antibody to aa496-515; P/N ratios of 9.2 (Ch1587) and 3.1 (Ch1601) at 1:1000 dilution (FIG. 4B). P/N ratio represents the optical density (OD) of the positive sample divided by the OD of a negative serum sample from the same animal.

The remaining samples were tested at 1:100 dilution. None of the chimpanzees that cleared HCV during primary or secondary infections had elevated levels of antibody to aa496-515 while only one of the chronically infected chimpanzees had slightly elevated levels, P/N ratio of 1.9 (FIG. 4C). A small proportion (6/54; 11%) of samples from chronically infected patients had P/N ratios≥2. No specific genotype was associated with positive signal. The samples with elevated signals≥3 were derived from patients infected with GT3a. To ensure that the serum samples were reactive in an ELISA, all samples were tested against additional peptides when tested for reactivity to peptide 496-515. The majority of the patient samples (n=45) were tested in a full Pepscan covering the entire E1 and E2 region. All of these sera reacted with multiple peptides in the Pepscan, even when no reactivity was observed with the 496-515 peptide. The remaining chimpanzee and patient samples were screened against a number of additional peptides: specifically, a peptide to 412-426; a peptide to HVR1 (H77, 1a sequence corresponding to the virus that was used to infect the chimpanzees); an NS3 peptide that represents a conserved epitope (aa1026-40); and a core peptide (aa28-42). All samples tested gave positive signals to at least one of these peptides (data not shown).

Vaccination of mice, chimpanzees, or humans with recombinant E1E2 proteins or synthetic peptides containing the aa496-515 region induces production of specific, cross neutralizing antibodies.

3.7. Neutralization with Antibodies Affinity Eluted from Chimpanzee Serum

In order to confirm aa496-515 as a neutralization epitope that can also be recognized by antibody from vaccines, we affinity eluted antibodies from Ch1587 serum using the aa496-515 peptide and tested the eluate ("AB-496") in a neutralization assay. As a positive control in these studies we used a peptide representing the EPI epitope (aa412-426) to affinity isolate antibodies from Ch1587 serum ("AB-412") and as negative controls we used peptides representing aa632-667 ("AB-632") and a Flu-M2 peptide to affinity isolate antibodies from Ch1587 serum. Antibodies recognizing aa632-667 had been shown to be non-neutralizing in our earlier mouse studies (FIGS. 2 and 3). The purity and specificity of the eluates were assessed by performing a Pepscan analysis. The affinity eluted samples only recognized the E2-specific peptides used for isolation while a range of peptides from this region were recognized by the unpurified Ch1587 serum (Ch1587-pos).

Figure 5:
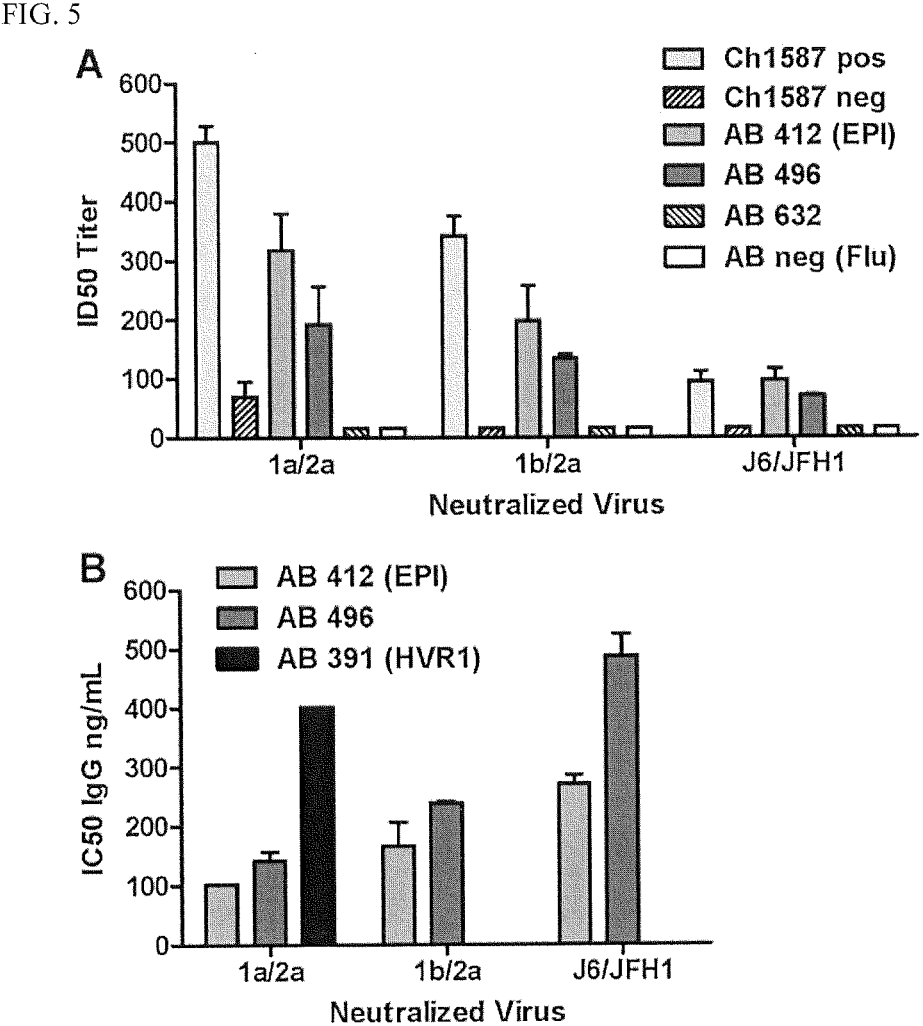
FIG. 5 presents histograms showing neutralization of HCVcc with affinity purified antibody. (A) ID50 titers against 1a/2a, 1b/2a, and J6/JFH1 of untreated serum from Ch1587 pre- (Ch1587-neg) and post- (Ch1587-pos) vaccination and affinity purified antibody from Ch1587-pos using specific peptides as noted. AB-neg represents the eluate from Ch1587-pos serum using Flu M2 peptide; AB-412 represents the eluate from Ch1587-pos serum using a peptide representing EPI (aa412-426); AB-632 represents the eluate from Ch1587-pos serum using a peptide representing HCV aa632-651, antibody to this epitope had been shown to be non-neutralizing. (B) IC50 titers of affinity purified AB-412 (EPI), AB-496, and AB-391 (HVR1) against 1a/2a, 1b/2a, and J6/JFH1 HCVcc. IC50 titers were calculated as the amount of IgG (ng/mL) required to neutralize 50% of the virus. Error bars represent standard error of the mean of replicates within one experiment. Neutralization assays were performed at least 3 times with similar results.

Results from the neutralization assays using these antibody samples are shown in FIG. 5. The untreated serum Ch1587-AB (Ch1587-pos) and AB-412 neutralized all three HCVcc (FIG. 5A). In addition, AB-496 was able to neutralize all three HCVcc, with ID50 titers of 202.9, 131.9 and 70.6 against 1a/2a, 1b/2a and J6/JFH1, respectively. The ID50 titers obtained for the negative control eluates, AB-neg and AB-632, were measured as <32 against all HCVcc and assigned titers of 1:16, the next lowest dilution. We did not obtain 90% neutralization at any dilution tested using the Ch1587-pos or the affinity purified antibodies.

We found that AB-412 had consistently higher ID50 titers than AB-496. To determine whether this was due to better binding of the antibody to the respective epitope or due to higher concentrations of the 412 antibody in the original serum sample leading to more efficient isolation, we assessed IgG, IgA and IgM concentrations in Ch1587-pos and in each eluate and determined the IC50 titer, the concentration of Ig (ng/mL) needed to neutralize 50% of the virus (FIG. 5B). In the unpurified sample (Ch1587-pos), the levels of IgA, IgM and IgG were calculated to be 0.011 mg/mL, 0.188 mg/mL and 65 mg/mL, respectively. For the affinity purified antibodies, AB-496 and AB-412, the signals for IgA and IgM were below the values of the standard curve at 1:50 dilution (i.e. ≤0.8 ng/mL in the original undiluted sample) while the amount of IgG was calculated to be about 24 ng/mL for both samples, i.e. at least 300-fold higher. The neutralizing activity in the affinity purified samples was concluded to be due to IgG antibody; therefore IC50 values are expressed as ng/mL of IgG. For both samples, more IgG was needed to neutralize 1b/2a and J6/JFH1 HCVcc than 1a/2a, presumably due to epitope variation. FIG. 5B shows that less of the antibody to aa412-426 was required to neutralize 50% of the virus compared to antibody recognizing aa496-515. The average IC50 titer for AB-412 derived from 2 separate isolations against 1a/2a was calculated as 102 ng/mL, while for AB-496 the average IC50 titer was calculated as 142 ng/mL. These values compared to an IC50 titer of 399 ng/mL for an HVR1-specific eluate isolated from the same Ch1587 plasma sample.

3.8. Mapping Antibodies to aa496-515 Using Chimpanzee Serum

Figure 6:
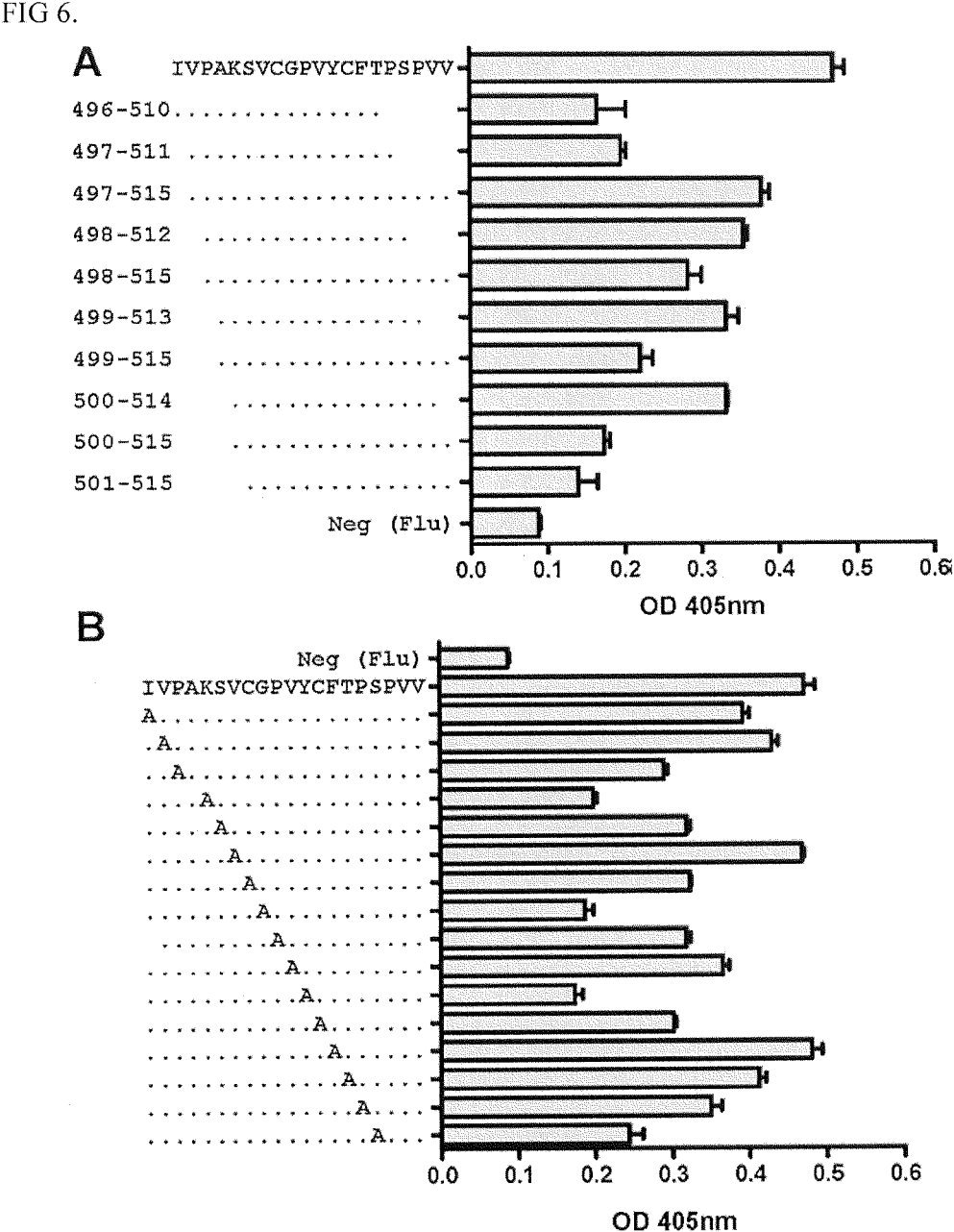
FIG. 6 presents histograms showing mapping of amino acids in the aa496-515 region involved in binding antibody. (A) is a histogram showing reactivity of affinity purified AB-496 (diluted 1:100) to overlapping 15mer peptides representing the aa496-515 epitope region, the sequence shown at the top of the figure (residues 496-515 of SEQ ID NO:1). (B) is a histogram showing reactivity of purified AB-496 (diluted 1:100) to 496-515 peptides containing single alanine substitutions. The aa496-515 epitope region sequence shown is residues 496-515 of SEQ ID NO:1. Error bars represent standard error of the mean of replicates within one experiment.

In order to more precisely map the aa496-515 epitope, we performed alanine scanning of the sequence and also synthesized a series of 15mer peptides for the region, overlapping by one residue. Binding results for the series of overlapping 15mers is shown in FIG. 6A. There were no mutations or truncations that led to complete abrogation of binding to affinity purified AB-496. However, both the carboxy and amino termini were important for efficient binding of antibody (FIG. 6A; peptides 496-510 and 501-515).

These observations were confirmed by alanine scanning using aa496-515 peptides with single residue ala substitutions. Results of the alanine scanning binding experiments are shown in FIG. 6B. Substitutions at the carboxy and amino termini impacted binding (residues 500 and 512) but in addition residues aa504 and 507 in the center of the epitope also reduced binding to less than 50% of that obtained using the wild type peptide (FIG. 6B). Similar effects were seen using unpurified Ch1587 serum, VVAB or SIN-AB, against the same mutated peptides (data not shown).

Figure 7:
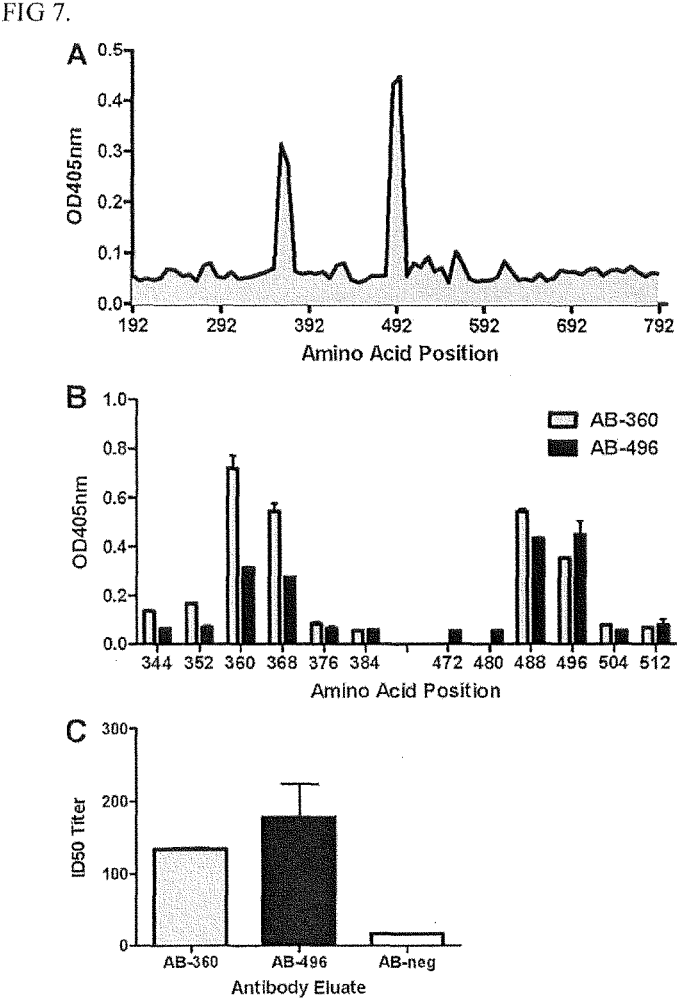
FIG. 7 presents the analysis of cross reactive region 344-403. (A) E1E2 Pepscan profile of affinity purified antibody AB-496 (diluted 1:400). (B) Cross-reactive ELISA signals obtained for affinity purified antibodies AB-360 and AB-496 when tested against peptides representing aa344-403 and aa472-531. Error bars represent standard error of the mean of replicates within one experiment. Assays were performed three times with similar results. (C) Neutralization of HCVcc chimera 1a/2a using antibody affinity purified with peptides representing aa360-387 (AB-360), aa496-515 (AB-496) and a negative Flu peptide (AB-neg). Error bars represent standard error of the mean of replicates within one experiment.
Figure 8:
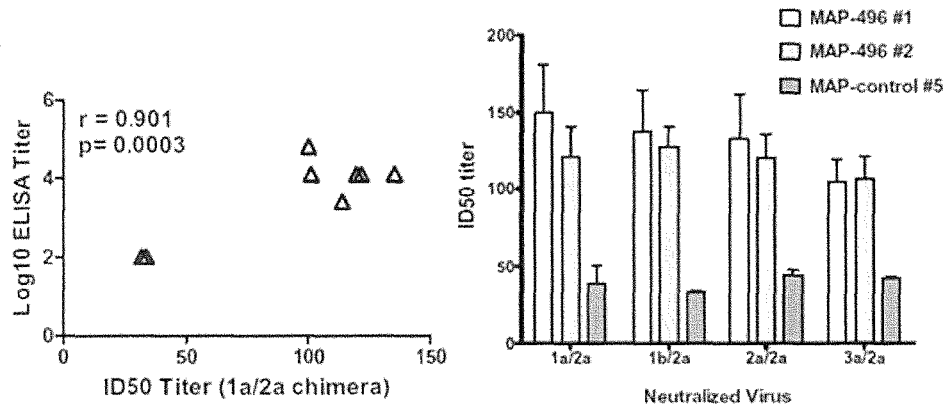
FIG. 8 shows serum titer data from mice immunized with a peptide representing aa496-515 of SEQ ID NO:1. (A) is a graph of the Log 10 ELISA titer against aa496-515 as a function of ID50 titer against the 1a/2a chimera. (B) is a histogram showing the ID50 titer for neutralization of various HCV types using polyclonal serum from 2 mice immunized with a peptide representing amino acids 496-515.
Figure 9:
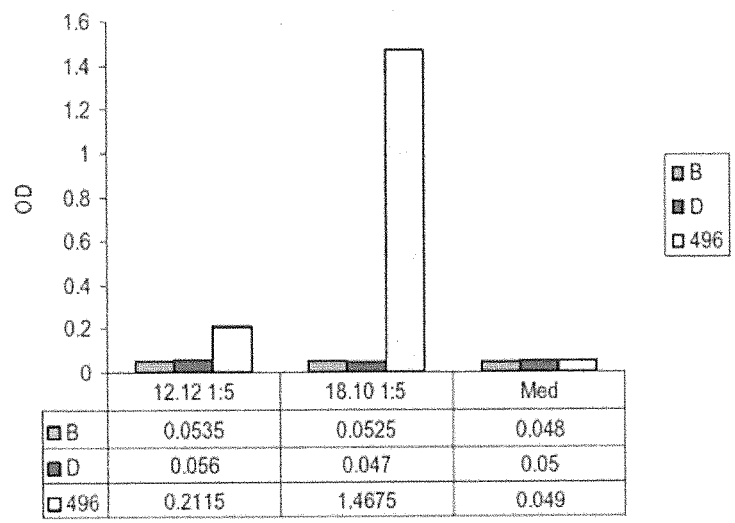

We also performed a full Pepscan analysis of isolated AB-496 using peptides representing both the E1 and E2 regions. In addition to recognizing peptides covering the aa496 region, the purified AB-496 eluate also reacted with 2 peptides in E1 representing aa360-387 (FIG. 7A). This cross recognition was reproducible with several individual AB-496 preparations. When the reverse antibody isolation experiment was performed using peptides representing aa360-387, the purified eluate recognized peptides covering the aa496 region (FIG. 7B). The purified AB-360 was also able to neutralize HCVcc 1a/2a, with an ID50 titer of 1:133, similar to AB-496 purified at the same time (1:178) (FIG. 7C). In terms of sequence similarity the two regions (aa360-387 and aa496-515) are highly diverse (only about 10% similarity), which excludes the possibility of cross reactivity based upon sequence homology. When considering charge and hydrophobicity, peptide 496 was found to have a net charge of +0.9 at pH 7 using a Hopp & Wood analysis, while the E1 aa360-387 peptide sequence was found to have a net charge of 0 at the same pH. Both peptides sequences contain 5-6 valine residues but the E1 region is substantially more hydrophobic, containing several leucine residues. The reactivity of the E1 peptides was specific to AB-496; no cross reactivity was seen between the peptides and AB-412 or AB-632 (data not shown). Therefore the hydrophobic nature of the peptide itself does not seem to be the cause of non-specific reactivity to Ig.

3.9 Multiple Antigen Peptide Immunizations.

In order to provide further evidence that antibodies to this region can cross neutralize, we immunized mice with a multiple antigen peptide (MAP) consisting of 4 branches, each representing aa496-515 (MAP-496) plus a poliovirus T-helper epitope, also synthesized on a 4-branch MAP resin (MAP Th). The MAP structures were synthesized by the Center for Biologics Core Facility using an ABI peptide synthesizer.

Eight groups of 5 mice were immunized subcutaneously at 0 and 4 weeks with combinations of a single epitope peptide (Pep-496), MAP-496, and MAP Th with and without Freund's adjuvant (CFA). For each immunization 10 ug of each peptide was used. Mice were bled at 2 weeks after the last dose and spleens harvested for T cell studies. As shown in the left panel of FIG. 15, MAP 496 peptide induced higher levels of specific antibodies during immunization than did PEP-496 (p=0.146, calculated with a Mann-Whitney test).

Figures 13, 14, 15:
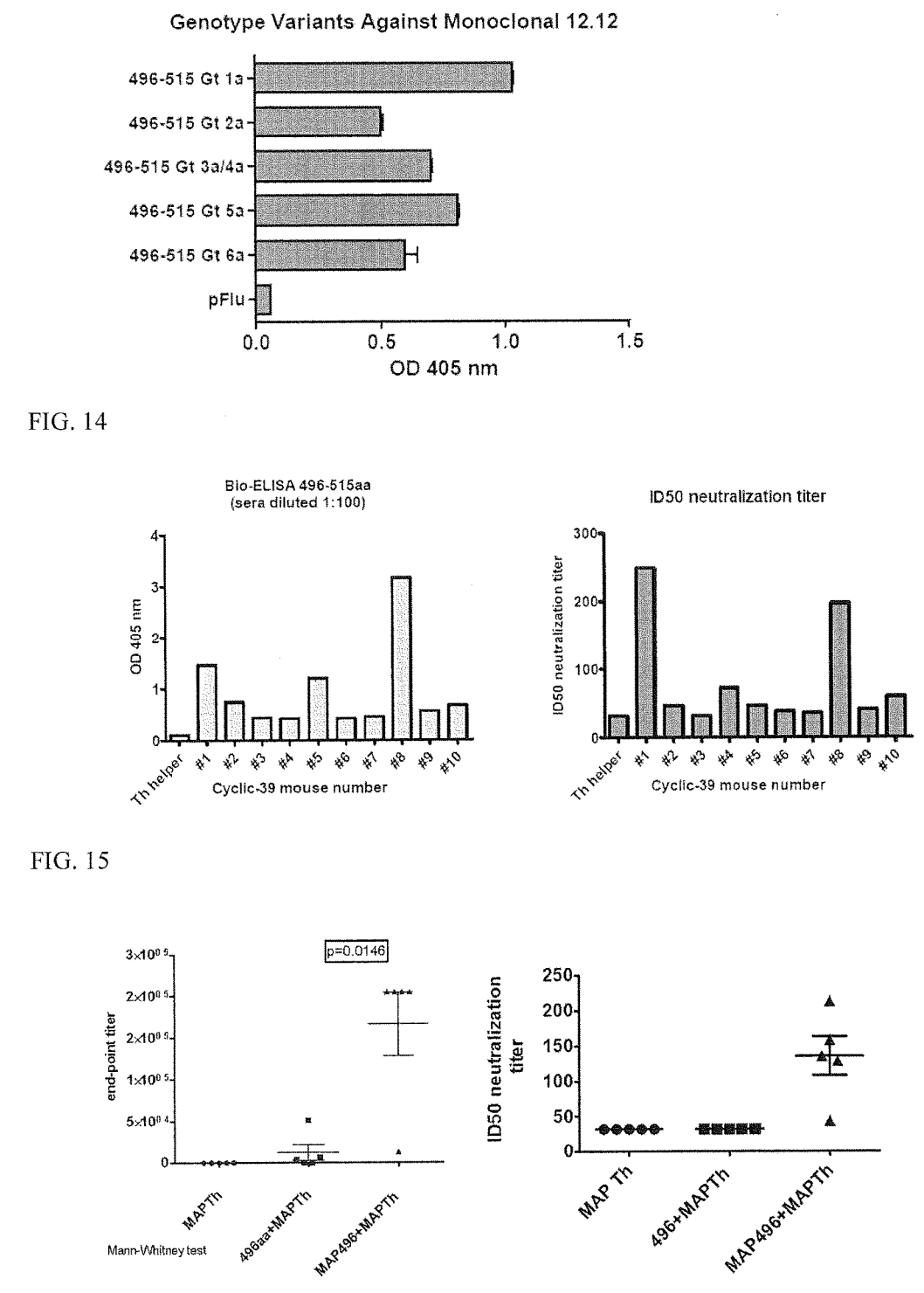

Additionally, as shown in the right panel of FIG. 15, MAP-496 induced the highest levels of neutralizing antibody to a 1a/2a chimeric HCVcc.

Example 2

Monoclonal Antibodies to HCV E2 aa 496-515

We immunized mice with a multiple antigen peptide (MAP) consisting of 4 branches, each representing aa496-515 ("Pep-39") of genotype 1a HCV (MAP-496), plus a poliovirus T-helper epitope, also synthesized on a 4-branch MAP resin (MAP Th), with CFA as an adjuvant Polyclonal serum from these mice contained high levels of anti-Pep-39 antibodies as assessed by ELISA and could cross neutralize different viral genotypes in vitro (FIG. 8)

Mice with highest levels of antibodies to Pep-39 were selected and spleen cells were fused with a myeloma cell line. These hybridomas were screened for anti-Pep-39 antibodies by ELISA. Media from positive wells were tested for in vitro neutralization activity against HCVcc 1a/2a chimera.

A subset of the positive wells were cloned by limiting dilution and isolated colonies were tested by ELISA. Two clones were selected, expanded, and used to make ascites in mice. These monoclonal antibodies were designated 12.12 and 18.10.

Representative neutralizing monoclonal antibodies 12.12 and 18.10 were further characterized.

Monoclonal antibodies 12.12 and 18.10 were each identified as having an IgG1 heavy chain isotype and a kappa light chain isotype.

Results of testing in ELISA against Pep-496 (representing aa496-515) and negative peptides (B and D) are shown in FIG. 9. Biotinylated peptides (1000 ng/well) were bound to streptavidin coated plates. Plates were blocked with 5% milk, then diluted MAbs were added. Anti-mouse horseradish peroxidase (HRP) was used as the secondary antibody for detection.

FIG. 9 shows that clone 18.10 showed a higher level of activity against peptide 496-515 in ELISA compared to clone 12.12, however the 18.10 monoclonal antibody prep used had a 4-fold higher IgG concentration than that of MAb 12.12. The data in FIG. 9 also show specific reactivity of both MAbs against the peptide 496-515; no reactivity is seen against the peptide B and D, two control peptides. The B peptide represents aa434-446 of and the D peptide represents aa412-426 the HCV polyprotein (SEQ ID NO:1).

To determine binding affinity of monoclonal antibodies 12.12 and 18.10 to peptide 495-515 aa, an end-point titration of binding of each antibody to the peptide was performed. Apparent binding affinity (K50) was determined from the titration as the half-maximal binding concentration of the antibody to the peptide. The apparent binding affinities determined are shown in Table 2.

TABLE 2

Apparent binding affinity to peptide 495-515 aa.

| MAb | $K_{50}$ (μg/mL) |
|---|---|
| 12.12 | 0.069 |
| 18.10 | 0.076 |

The nucleotide sequence of the variable region of the light and heavy chains was also determined for each of monoclonal antibodies 12.12 and 18.10. Sequences are identified in Table 3.

TABLE 3

| | Nucleotide sequence SEQ ID NO. | Amino acid sequence SEQ ID NO |
|---|---|---|
| MAb 12.12 Heavy chain variable region | 2 | 3 |
| MAb 12.12 Kappa chain variable region | 4 | 5 |
| MAb 18.10 Heavy chain variable region | 6 | 7 |
| MAb 18.10 Kappa chain variable region | 8 | 9 |

Nucleotide sequence results were aligned and analyzed using IMGT/V-QUEST (Brochet, X. et al., Nucl. Acids Res, 36, W503-508 (2008)), available on the interne from IIMGT®, the International ImMunoGeneTics Information System® Lefranc, M.-P., et al. Nucl. Acids Res, 37, D1006-D1012 (2009)). Nucleotide sequences of the heavy chain and the light (kappa) chain of MAb 12.12 are SEQ ID NOS:

2 and 4, respectively, while nucleotide sequences of the heavy chain and the light (kappa) chain of MAb 18.10 are SEQ ID NOS: 6 and 8, respectively. Translation of the nucleotide sequences yields protein sequences of the heavy chain and the light (kappa) chains for each monoclonal antibody. The amino acid sequences of the CDRs for monoclonal antibodies 12.12 and 18.10 determined by IMGT/V-QUEST are shown in Table 4

TABLE 4

| MAb 12.12 | | | |
|---|---|---|---|
| Region | Amino acid sequence | SEQ ID NO. | aa residues |
| Heavy chain CDR1 | GFTFSSFG | 3 | 27-34 |
| Heavy chain CDR2 | ISSGSSTL | 3 | 52-59 |
| Heavy chain CDR3 | DHGHRLLK | 3 | 98-105 |
| Kappa chain CDR1 | QDVGTA | 5 | 27-32 |
| Kappa chain CDR2 | WAS | 5 | 50-52 |
| Kappa chain CDR3 | QQYSNFPLT | 5 | 89-97 |

| MAb 18.10 | | | |
|---|---|---|---|
| Region | Amino acid sequence | SEQ ID NO. | aa residues |
| Heavy chain CDR1 | GYSITSDYA | 7 | 27-35 |
| Heavy chain CDR2 | IGYSGNT | 7 | 53-59 |
| Heavy chain CDR3 | SAVDGSY | 7 | 98-104 |
| Kappa chain CDR1 | LNLGTP | 9 | 27-32 |
| Kappa chain CDR2 | RTA | 9 | 50-52 |
| Kappa chain CDR3 | EKDGYYPLT | 9 | 89-97 |

Example 3

Neutralizing Activity of Monoclonal Antibodies 18.10 and 12.12

Figure 10:
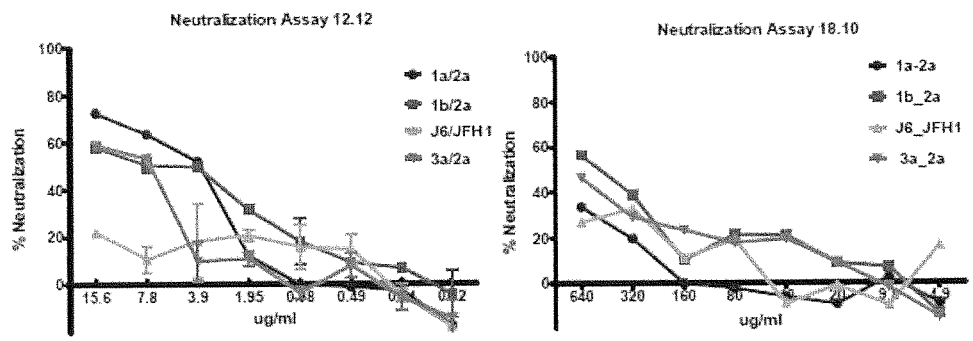
FIG. 10 presents graphs showing neutralization of chimeric HCVcc with monoclonal antibodies 12.12 (left panel) or 18.10 (right panel).

A 2-fold dilution series was performed for monoclonal antibodies 12.12 and 18.10, starting at 1:32. Dilutions were tested for neutralizing activity against HCVcc expressing the GT 1a, 1b, 2a and 3a envelope proteins on the particle surface (1a/2a, 1b/2a, J6/JFH1 and 3a/2a, respectively in FIG. 10).

Monoclonal antibody (MAb) 12.12 was able to neutralize all chimeric viruses except J6/JFH1 (2a envelope) in a dose dependent fashion. MAb 18.10 was found to be poorly neutralizing despite the use of much higher amounts of IgG for the neutralization assay. Starting concentration was 640 ug/mL compared to 15 ug/mL for MAb 12.12.

Figure 11:
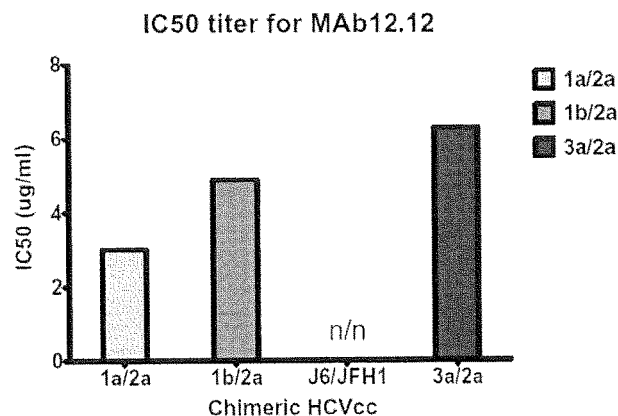
FIG. 11 presents a histogram showing IC50 titers for MAb 12.12 against chimeric HCVcc. In the figure, n/n=non-neutralizing.

FIG. 11 shows the calculated IC50 values for MAb 12.12 against the chimeric HCVcc. IC50 represents the concentration of antibody in ug/mL needed to neutralize 50% of the virus. The highest IC50 was obtained against the 1a/2a chimeric virus that has the identical amino acid sequence in the region 496-515 as that used for immunization. No titer could be calculated for J6/JFH1 as neutralization did not reach 50% even at the highest concentration of antibody used.

Example 4

Mapping Residues for Monoclonal Antibody Binding

Residues involved in monoclonal antibody binding were mapped by alanine scanning and random phage display.

Figure 12:
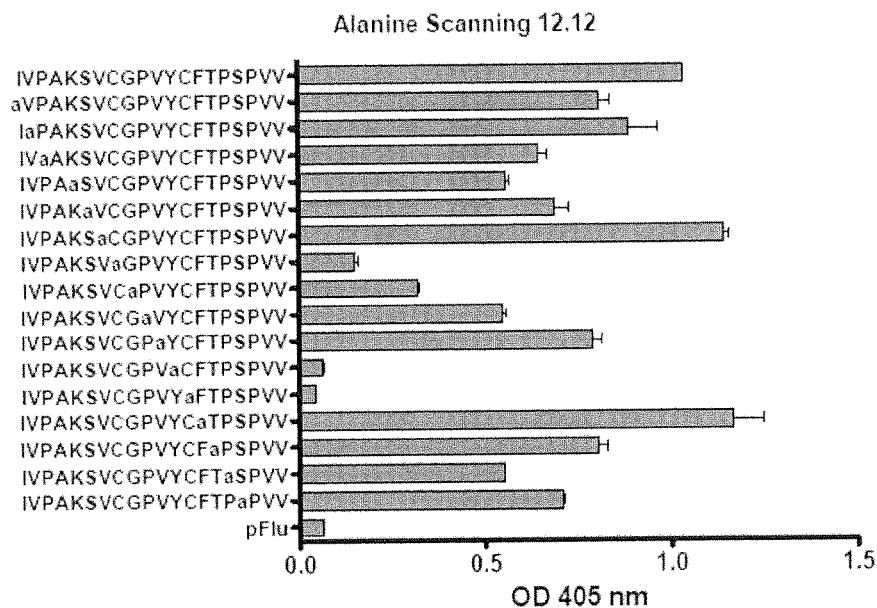
FIG. 12 is a histogram showing binding of monoclonal antibody 12.12 to singly alanine-substituted peptides based on aa496-515 of SEQ ID NO:1. The top sequence in the figure is the unsubstituted peptide of sequence aa496-515 of SEQ ID NO:1.

Monoclonal antibody 12.12 was tested against peptides with Alanine substitutions at single residue sites across the linear sequence. The reduction in signal to specific peptides indicates which residues are important for binding. The binding of the monoclonal antibody 12.12 is shown in FIG. 12. The residues important for binding are in the region CGPVYC (residues 503-508 of SEQ ID NO:1) of the 496 to 515 sequence (IVPAKSVCGPVYCFTPSPVV) of SEQ ID NO:1.

Monoclonal 12.12 was also tested against a random phage display library to identify the major binding site. The results of the phage display studies showed that the GPVY sequence (residues 504-507 of SEQ ID NO: 1) in E2, which is flanked by cysteine residues, was identified as important for binding, consistent with the binding residues identified through Alanine scanning. Several sequences in which V-506 was substituted with leucine and/or Y-507 was substituted with phenylalanine or tryptopham were also observed to bind to the antibody.

We tested the binding of the monoclonal 12.12 to linear peptides representing sequences from other HCV genotypes (FIG. 13). The binding was reduced slightly to all genotype variants with the greatest reduction seen against the 2a peptide.

Example 5

Immunization of Mice with Cyclized 496-515 Epitope

Krey et al. (Krey T, et al. (2010) PLoS Pathog 6(2): e1000762. doi:10.1371/journal.ppat.1000762, 11 pages) proposed a tertiary structure for HCV E2 protein, including the 496-515 epitope region. In order to mimic the structure of the 496-515 epitope region proposed by Krey et al., we cyclized a 496-515 epitope peptide by forming a disulfide bridge between the two cysteine residues of the peptide. The cyclized peptide ("cyclic-39") was then used for mouse immunizations to produce antibodies. FIG. 14 shows the results of an ELISA assay and an ID50 neutralization assay of sera from several mice.

Example 6

Immunization of Humans with rE1E2

A panel of about 100 uninfected human subjects is vaccinated with recombinant E1E2 protein adjuvanted with MF59C.1 or with placebo. Serum samples from the subjects are tested in ELISA for induction of antibodies to the aa496-515 epitope and level of induction for the two groups is compared. Antibodies to the aa496-515 epitope are induced in the subjects vaccinated with rE1E2 at a significantly higher level than in the group vaccinated with placebo.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). The modifier "about" used in connection with a quantity is inclusive of the stated value and has the meaning dictated by the context (e.g., includes the degree of error associated with measurement of the particular quantity).

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

Unless defined otherwise, technical and scientific terms used herein have the same meaning as is commonly understood by one of skill in the art to which this invention belongs.

All references are incorporated by reference herein.

Embodiments of this invention are described herein, including the best mode known to the inventors for carrying out the invention. Variations of these embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated antibody, which binds specifically to an epitope of hepatitis C virus (HCV),
   wherein the epitope is contained within amino acid residues 496-515 of the HCV polyprotein set forth in SEQ ID NO:1,
   the antibody comprising
   a heavy chain variable region comprising complementary determining region (CDR) 1 amino acid sequence of residues 27-34 (GFTFSSFG) of SEQ ID NO:3, CDR2 amino acid sequence of residues 52-59 (ISSGSSTL) of SEQ ID NO:3, and CDR3 amino acid sequence of residues 98-105 (DHGHRLLK) of SEQ ID NO:3, and
   a light chain variable region comprising CDR1 amino acid sequence of residues 27-32 (QDVGTA) of SEQ ID NO:5, CDR2 amino acid sequence of residues 50-52 (WAS) of SEQ ID NO:5, and CDR3 amino acid sequence of residues 89-97 (QQYSNFPLT) of SEQ ID NO:5.

2. The isolated antibody of claim 1, wherein the epitope is amino acid residues 504-507 of SEQ ID NO:1.

3. The isolated antibody of claim 1, wherein the antibody is a monoclonal antibody, a polyclonal antibody, a chimeric antibody, a humanized antibody, a synthetic antibody, or an antigen-binding antibody fragment.

4. The isolated antibody of claim 1 that is a humanized antibody.

5. The isolated antibody of claim 1, comprising a heavy chain variable region comprising an amino acid sequence consisting of SEQ ID NO:3 or encoded by a polynucleotide comprising SEQ ID NO:2.

6. The isolated antibody of claim 1, comprising a light chain variable region comprising an amino acid sequence consisting of SEQ ID NO:5 or encoded by a polynucleotide comprising SEQ ID NO:4.

7. A composition comprising
   the antibody of claim 1; and
   a pharmaceutically acceptable carrier, a toxic material, a solid support, a carrier molecule, a chemotherapeutic agent, or a labeling material.

8. A method of detecting a hepatitis C virus (HCV) epitope in a sample comprising
   contacting the antibody of claim 1 with a sample under conditions such that the antibody binds an epitope of hepatitis C virus (HCV); and
   detecting the HCV epitope in the sample by detecting antibody bound to the epitope.

9. A method for treatment of or prophylaxis against Hepatitis C Virus (HCV) infection comprising
   administering the antibody according to claim 1 to a subject prior to or after exposure to Hepatitis C Virus (HCV).

10. The method of claim 9, wherein the subject is a liver transplant patient.

11. The antibody of claim 1, wherein the antibody is a monoclonal antibody.

12. The antibody of claim 1, wherein the antibody is a chimeric antibody.

13. The antibody of claim 1, wherein the antibody is linked to a toxic material, a solid support, a carrier molecule, or a labeling material.

* * * * *

SEQUENCE LISTING

```
<160> NUMBER OF SEQ ID NOS: 9

<210> SEQ ID NO 1
<211> LENGTH: 3011
<212> TYPE: PRT
<213> ORGANISM: Hepatitis C virus

<400> SEQUENCE: 1

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255
```

-continued

```
Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Glu
    370                 375                 380

Thr His Val Thr Gly Gly Ser Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430

Leu Asn Thr Gly Trp Leu Ala Gly Leu Phe Tyr Gln His Lys Phe Asn
        435                 440                 445

Ser Ser Gly Cys Pro Glu Arg Leu Ala Ser Cys Arg Arg Leu Thr Asp
    450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Arg Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Ala Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
                565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
        595                 600                 605

Val Asp Tyr Pro Tyr Arg Leu Trp His Tyr Pro Cys Thr Ile Asn Tyr
    610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
```

675                 680                 685
Leu Ile His Leu His Gln Asn Ile Val Asp Val Gln Tyr Leu Tyr Gly
                690                 695                 700
Val Gly Ser Ser Ile Ala Ser Trp Ala Ile Lys Trp Glu Tyr Val Val
705                 710                 715                 720
Leu Leu Phe Leu Leu Leu Ala Asp Ala Arg Val Cys Ser Cys Leu Trp
                725                 730                 735
Met Met Leu Leu Ile Ser Gln Ala Glu Ala Ala Leu Glu Asn Leu Val
                740                 745                 750
Ile Leu Asn Ala Ala Ser Leu Ala Gly Thr His Gly Leu Val Ser Phe
                755                 760                 765
Leu Val Phe Phe Cys Phe Ala Trp Tyr Leu Lys Gly Arg Trp Val Pro
            770                 775                 780
Gly Ala Val Tyr Ala Phe Tyr Gly Met Trp Pro Leu Leu Leu Leu Leu
785                 790                 795                 800
Leu Ala Leu Pro Gln Arg Ala Tyr Ala Leu Asp Thr Glu Val Ala Ala
                805                 810                 815
Ser Cys Gly Gly Val Val Leu Val Gly Leu Met Ala Leu Thr Leu Ser
                820                 825                 830
Pro Tyr Tyr Lys Arg Tyr Ile Ser Trp Cys Met Trp Trp Leu Gln Tyr
                835                 840                 845
Phe Leu Thr Arg Val Glu Ala Gln Leu His Val Trp Val Pro Pro Leu
850                 855                 860
Asn Val Arg Gly Gly Arg Asp Ala Val Ile Leu Leu Met Cys Val Val
865                 870                 875                 880
His Pro Thr Leu Val Phe Asp Ile Thr Lys Leu Leu Leu Ala Ile Phe
                885                 890                 895
Gly Pro Leu Trp Ile Leu Gln Ala Ser Leu Leu Lys Val Pro Tyr Phe
                900                 905                 910
Val Arg Val Gln Gly Leu Leu Arg Ile Cys Ala Leu Ala Arg Lys Ile
                915                 920                 925
Ala Gly Gly His Tyr Val Gln Met Ala Ile Ile Lys Leu Gly Ala Leu
            930                 935                 940
Thr Gly Thr Tyr Val Tyr Asn His Leu Thr Pro Leu Arg Asp Trp Ala
945                 950                 955                 960
His Asn Gly Leu Arg Asp Leu Ala Val Ala Val Glu Pro Val Val Phe
                965                 970                 975
Ser Arg Met Glu Thr Lys Leu Ile Thr Trp Gly Ala Asp Thr Ala Ala
                980                 985                 990
Cys Gly Asp Ile Ile Asn Gly Leu Pro Val Ser Ala Arg Arg Gly Gln
            995                 1000                1005
Glu Ile Leu Leu Gly Pro Ala Asp Gly Met Val Ser Lys Gly Trp
        1010                1015                1020
Arg Leu Leu Ala Pro Ile Thr Ala Tyr Ala Gln Gln Thr Arg Gly
        1025                1030                1035
Leu Leu Gly Cys Ile Ile Thr Ser Leu Thr Gly Arg Asp Lys Asn
        1040                1045                1050
Gln Val Glu Gly Glu Val Gln Ile Val Ser Thr Ala Thr Gln Thr
        1055                1060                1065
Phe Leu Ala Thr Cys Ile Asn Gly Val Cys Trp Thr Val Tyr His
        1070                1075                1080
Gly Ala Gly Thr Arg Thr Ile Ala Ser Pro Lys Gly Pro Val Ile
        1085                1090                1095

-continued

Gln Met Tyr Thr Asn Val Asp Gln Asp Leu Val Gly Trp Pro Ala
1100                1105                1110

Pro Gln Gly Ser Arg Ser Leu Thr Pro Cys Thr Cys Gly Ser Ser
1115                1120                1125

Asp Leu Tyr Leu Val Thr Arg His Ala Asp Val Ile Pro Val Arg
1130                1135                1140

Arg Arg Gly Asp Ser Arg Gly Ser Leu Leu Ser Pro Arg Pro Ile
1145                1150                1155

Ser Tyr Leu Lys Gly Ser Ser Gly Gly Pro Leu Leu Cys Pro Ala
1160                1165                1170

Gly His Ala Val Gly Leu Phe Arg Ala Ala Val Cys Thr Arg Gly
1175                1180                1185

Val Ala Lys Ala Val Asp Phe Ile Pro Val Glu Asn Leu Glu Thr
1190                1195                1200

Thr Met Arg Ser Pro Val Phe Thr Asp Asn Ser Ser Pro Pro Ala
1205                1210                1215

Val Pro Gln Ser Phe Gln Val Ala His Leu His Ala Pro Thr Gly
1220                1225                1230

Ser Gly Lys Ser Thr Lys Val Pro Ala Ala Tyr Ala Ala Gln Gly
1235                1240                1245

Tyr Lys Val Leu Val Leu Asn Pro Ser Val Ala Ala Thr Leu Gly
1250                1255                1260

Phe Gly Ala Tyr Met Ser Lys Ala His Gly Val Asp Pro Asn Ile
1265                1270                1275

Arg Thr Gly Val Arg Thr Ile Thr Thr Gly Ser Pro Ile Thr Tyr
1280                1285                1290

Ser Thr Tyr Gly Lys Phe Leu Ala Asp Gly Gly Cys Ser Gly Gly
1295                1300                1305

Ala Tyr Asp Ile Ile Ile Cys Asp Glu Cys His Ser Thr Asp Ala
1310                1315                1320

Thr Ser Ile Leu Gly Ile Gly Thr Val Leu Asp Gln Ala Glu Thr
1325                1330                1335

Ala Gly Ala Arg Leu Val Val Leu Ala Thr Ala Thr Pro Pro Gly
1340                1345                1350

Ser Val Thr Val Ser His Pro Asn Ile Glu Glu Val Ala Leu Ser
1355                1360                1365

Thr Thr Gly Glu Ile Pro Phe Tyr Gly Lys Ala Ile Pro Leu Glu
1370                1375                1380

Val Ile Lys Gly Gly Arg His Leu Ile Phe Cys His Ser Lys Lys
1385                1390                1395

Lys Cys Asp Glu Leu Ala Ala Lys Leu Val Ala Leu Gly Ile Asn
1400                1405                1410

Ala Val Ala Tyr Tyr Arg Gly Leu Asp Val Ser Val Ile Pro Thr
1415                1420                1425

Ser Gly Asp Val Val Val Ser Thr Asp Ala Leu Met Thr Gly
1430                1435                1440

Phe Thr Gly Asp Phe Asp Ser Val Ile Asp Cys Asn Thr Cys Val
1445                1450                1455

Thr Gln Thr Val Asp Phe Ser Leu Asp Pro Thr Phe Thr Ile Glu
1460                1465                1470

Thr Thr Thr Leu Pro Gln Asp Ala Val Ser Arg Thr Gln Arg Arg
1475                1480                1485

```
Gly Arg Thr Gly Arg Gly Lys Pro Gly Ile Tyr Arg Phe Val Ala
1490                1495                1500

Pro Gly Glu Arg Pro Ser Gly Met Phe Asp Ser Ser Val Leu Cys
1505                1510                1515

Glu Cys Tyr Asp Ala Gly Cys Ala Trp Tyr Glu Leu Thr Pro Ala
1520                1525                1530

Glu Thr Thr Val Arg Leu Arg Ala Tyr Met Asn Thr Pro Gly Leu
1535                1540                1545

Pro Val Cys Gln Asp His Leu Glu Phe Trp Glu Gly Val Phe Thr
1550                1555                1560

Gly Leu Thr His Ile Asp Ala His Phe Leu Ser Gln Thr Lys Gln
1565                1570                1575

Ser Gly Glu Asn Phe Pro Tyr Leu Val Ala Tyr Gln Ala Thr Val
1580                1585                1590

Cys Ala Arg Ala Gln Ala Pro Pro Pro Ser Trp Asp Gln Met Trp
1595                1600                1605

Lys Cys Leu Ile Arg Leu Lys Pro Thr Leu His Gly Pro Thr Pro
1610                1615                1620

Leu Leu Tyr Arg Leu Gly Ala Val Gln Asn Glu Val Thr Leu Thr
1625                1630                1635

His Pro Ile Thr Lys Tyr Ile Met Thr Cys Met Ser Ala Asp Leu
1640                1645                1650

Glu Val Val Thr Ser Thr Trp Val Leu Val Gly Gly Val Leu Ala
1655                1660                1665

Ala Leu Ala Ala Tyr Cys Leu Ser Thr Gly Cys Val Val Ile Val
1670                1675                1680

Gly Arg Ile Val Leu Ser Gly Lys Pro Ala Ile Ile Pro Asp Arg
1685                1690                1695

Glu Val Leu Tyr Gln Glu Phe Asp Glu Met Glu Glu Cys Ser Gln
1700                1705                1710

His Leu Pro Tyr Ile Glu Gln Gly Met Met Leu Ala Glu Gln Phe
1715                1720                1725

Lys Gln Lys Ala Leu Gly Leu Leu Gln Thr Ala Ser Arg Gln Ala
1730                1735                1740

Glu Val Ile Thr Pro Ala Val Gln Thr Asn Trp Gln Lys Leu Glu
1745                1750                1755

Val Phe Trp Ala Lys His Met Trp Asn Phe Ile Ser Gly Ile Gln
1760                1765                1770

Tyr Leu Ala Gly Leu Ser Thr Leu Pro Gly Asn Pro Ala Ile Ala
1775                1780                1785

Ser Leu Met Ala Phe Thr Ala Ala Val Thr Ser Pro Leu Thr Thr
1790                1795                1800

Gly Gln Thr Leu Leu Phe Asn Ile Leu Gly Gly Trp Val Ala Ala
1805                1810                1815

Gln Leu Ala Ala Pro Gly Ala Ala Thr Ala Phe Val Gly Ala Gly
1820                1825                1830

Leu Ala Gly Ala Ala Ile Gly Ser Val Gly Leu Gly Lys Val Leu
1835                1840                1845

Val Asp Ile Leu Ala Gly Tyr Gly Ala Gly Val Ala Gly Ala Leu
1850                1855                1860

Val Ala Phe Lys Ile Met Ser Gly Glu Val Pro Ser Thr Glu Asp
1865                1870                1875

Leu Val Asn Leu Leu Pro Ala Ile Leu Ser Pro Gly Ala Leu Val
```

-continued

```
            1880                1885                1890
Val Gly Val Val Cys Ala Ala Ile Leu Arg Arg His Val Gly Pro
            1895                1900                1905
Gly Glu Gly Ala Val Gln Trp Met Asn Arg Leu Ile Ala Phe Ala
            1910                1915                1920
Ser Arg Gly Asn His Val Ser Pro Thr His Tyr Val Pro Glu Ser
            1925                1930                1935
Asp Ala Ala Ala Arg Val Thr Ala Ile Leu Ser Ser Leu Thr Val
            1940                1945                1950
Thr Gln Leu Leu Arg Arg Leu His Gln Trp Ile Ser Ser Glu Cys
            1955                1960                1965
Thr Thr Pro Cys Ser Gly Ser Trp Leu Arg Asp Ile Trp Asp Trp
            1970                1975                1980
Ile Cys Glu Val Leu Ser Asp Phe Lys Thr Trp Leu Lys Ala Lys
            1985                1990                1995
Leu Met Pro Gln Leu Pro Gly Ile Pro Phe Val Ser Cys Gln Arg
            2000                2005                2010
Gly Tyr Arg Gly Val Trp Arg Gly Asp Gly Ile Met His Thr Arg
            2015                2020                2025
Cys His Cys Gly Ala Glu Ile Thr Gly His Val Lys Asn Gly Thr
            2030                2035                2040
Met Arg Ile Val Gly Pro Arg Thr Cys Arg Asn Met Trp Ser Gly
            2045                2050                2055
Thr Phe Pro Ile Asn Ala Tyr Thr Thr Gly Pro Cys Thr Pro Leu
            2060                2065                2070
Pro Ala Pro Asn Tyr Lys Phe Ala Leu Trp Arg Val Ser Ala Glu
            2075                2080                2085
Glu Tyr Val Glu Ile Arg Arg Val Gly Asp Phe His Tyr Val Ser
            2090                2095                2100
Gly Met Thr Thr Asp Asn Leu Lys Cys Pro Cys Gln Ile Pro Ser
            2105                2110                2115
Pro Glu Phe Phe Thr Glu Leu Asp Gly Val Arg Leu His Arg Phe
            2120                2125                2130
Ala Pro Pro Cys Lys Pro Leu Leu Arg Glu Glu Val Ser Phe Arg
            2135                2140                2145
Val Gly Leu His Glu Tyr Pro Val Gly Ser Gln Leu Pro Cys Glu
            2150                2155                2160
Pro Glu Pro Asp Val Ala Val Leu Thr Ser Met Leu Thr Asp Pro
            2165                2170                2175
Ser His Ile Thr Ala Glu Ala Ala Gly Arg Arg Leu Ala Arg Gly
            2180                2185                2190
Ser Pro Pro Ser Met Ala Ser Ser Ser Ala Ser Gln Leu Ser Ala
            2195                2200                2205
Pro Ser Leu Lys Ala Thr Cys Thr Ala Asn His Asp Ser Pro Asp
            2210                2215                2220
Ala Glu Leu Ile Glu Ala Asn Leu Leu Trp Arg Gln Glu Met Gly
            2225                2230                2235
Gly Asn Ile Thr Arg Val Glu Ser Glu Asn Lys Val Val Ile Leu
            2240                2245                2250
Asp Ser Phe Asp Pro Leu Val Ala Glu Glu Asp Glu Arg Glu Val
            2255                2260                2265
Ser Val Pro Ala Glu Ile Leu Arg Lys Ser Arg Arg Phe Ala Arg
            2270                2275                2280
```

```
Ala Leu Pro Val Trp Ala Arg Pro Asp Tyr Asn Pro Pro Leu Val
    2285            2290            2295

Glu Thr Trp Lys Lys Pro Asp Tyr Glu Pro Pro Val Val His Gly
    2300            2305            2310

Cys Pro Leu Pro Pro Arg Ser Pro Val Pro Pro Pro Arg
    2315            2320            2325

Lys Lys Arg Thr Val Val Leu Thr Glu Ser Thr Leu Ser Thr Ala
    2330            2335            2340

Leu Ala Glu Leu Ala Thr Lys Ser Phe Gly Ser Ser Ser Thr Ser
    2345            2350            2355

Gly Ile Thr Gly Asp Asn Thr Thr Thr Ser Ser Glu Pro Ala Pro
    2360            2365            2370

Ser Gly Cys Pro Pro Asp Ser Asp Val Glu Ser Tyr Ser Ser Met
    2375            2380            2385

Pro Pro Leu Glu Gly Glu Pro Gly Asp Pro Asp Leu Ser Asp Gly
    2390            2395            2400

Ser Trp Ser Thr Val Ser Ser Gly Ala Asp Thr Glu Asp Val Val
    2405            2410            2415

Cys Cys Ser Met Ser Tyr Ser Trp Thr Gly Ala Leu Val Thr Pro
    2420            2425            2430

Cys Ala Ala Glu Glu Gln Lys Leu Pro Ile Asn Ala Leu Ser Asn
    2435            2440            2445

Ser Leu Leu Arg His His Asn Leu Val Tyr Ser Thr Thr Ser Arg
    2450            2455            2460

Ser Ala Cys Gln Arg Gln Lys Lys Val Thr Phe Asp Arg Leu Gln
    2465            2470            2475

Val Leu Asp Ser His Tyr Gln Asp Val Leu Lys Glu Val Lys Ala
    2480            2485            2490

Ala Ala Ser Lys Val Lys Ala Asn Leu Leu Ser Val Glu Glu Ala
    2495            2500            2505

Cys Ser Leu Thr Pro Pro His Ser Ala Lys Ser Lys Phe Gly Tyr
    2510            2515            2520

Gly Ala Lys Asp Val Arg Cys His Ala Arg Lys Ala Val Ala His
    2525            2530            2535

Ile Asn Ser Val Trp Lys Asp Leu Leu Glu Asp Ser Val Thr Pro
    2540            2545            2550

Ile Asp Thr Thr Ile Met Ala Lys Asn Glu Val Phe Cys Val Gln
    2555            2560            2565

Pro Glu Lys Gly Gly Arg Lys Pro Ala Arg Leu Ile Val Phe Pro
    2570            2575            2580

Asp Leu Gly Val Arg Val Cys Glu Lys Met Ala Leu Tyr Asp Val
    2585            2590            2595

Val Ser Lys Leu Pro Leu Ala Val Met Gly Ser Ser Tyr Gly Phe
    2600            2605            2610

Gln Tyr Ser Pro Gly Gln Arg Val Glu Phe Leu Val Gln Ala Trp
    2615            2620            2625

Lys Ser Lys Lys Thr Pro Met Gly Phe Ser Tyr Asp Thr Arg Cys
    2630            2635            2640

Phe Asp Ser Thr Val Thr Glu Ser Asp Ile Arg Thr Glu Glu Ala
    2645            2650            2655

Ile Tyr Gln Cys Cys Asp Leu Asp Pro Gln Ala Arg Val Ala Ile
    2660            2665            2670
```

```
Lys Ser Leu Thr Glu Arg Leu Tyr Val Gly Gly Pro Leu Thr Asn
    2675                2680                2685
Ser Arg Gly Glu Asn Cys Gly Tyr Arg Arg Cys Arg Ala Ser Gly
    2690                2695                2700
Val Leu Thr Thr Ser Cys Gly Asn Thr Leu Thr Cys Tyr Ile Lys
    2705                2710                2715
Ala Arg Ala Ala Cys Arg Ala Ala Gly Leu Gln Asp Cys Thr Met
    2720                2725                2730
Leu Val Cys Gly Asp Asp Leu Val Val Ile Cys Glu Ser Ala Gly
    2735                2740                2745
Val Gln Glu Asp Ala Ala Ser Leu Arg Ala Phe Thr Glu Ala Met
    2750                2755                2760
Thr Arg Tyr Ser Ala Pro Pro Gly Asp Pro Gln Pro Glu Tyr
    2765                2770                2775
Asp Leu Glu Leu Ile Thr Ser Cys Ser Ser Asn Val Ser Val Ala
    2780                2785                2790
His Asp Gly Ala Gly Lys Arg Val Tyr Tyr Leu Thr Arg Asp Pro
    2795                2800                2805
Thr Thr Pro Leu Ala Arg Ala Ala Trp Glu Thr Ala Arg His Thr
    2810                2815                2820
Pro Val Asn Ser Trp Leu Gly Asn Ile Ile Met Phe Ala Pro Thr
    2825                2830                2835
Leu Trp Ala Arg Met Ile Leu Met Thr His Phe Phe Ser Val Leu
    2840                2845                2850
Ile Ala Arg Asp Gln Leu Glu Gln Ala Leu Asn Cys Glu Ile Tyr
    2855                2860                2865
Gly Ala Cys Tyr Ser Ile Glu Pro Leu Asp Leu Pro Pro Ile Ile
    2870                2875                2880
Gln Arg Leu His Gly Leu Ser Ala Phe Ser Leu His Ser Tyr Ser
    2885                2890                2895
Pro Gly Glu Ile Asn Arg Val Ala Ala Cys Leu Arg Lys Leu Gly
    2900                2905                2910
Val Pro Pro Leu Arg Ala Trp Arg His Arg Ala Arg Ser Val Arg
    2915                2920                2925
Ala Arg Leu Leu Ser Arg Gly Gly Arg Ala Ala Ile Cys Gly Lys
    2930                2935                2940
Tyr Leu Phe Asn Trp Ala Val Arg Thr Lys Leu Lys Leu Thr Pro
    2945                2950                2955
Ile Ala Ala Ala Gly Arg Leu Asp Leu Ser Gly Trp Phe Thr Ala
    2960                2965                2970
Gly Tyr Ser Gly Gly Asp Ile Tyr His Ser Val Ser His Ala Arg
    2975                2980                2985
Pro Arg Trp Phe Trp Phe Cys Leu Leu Leu Leu Ala Ala Gly Val
    2990                2995                3000
Gly Ile Tyr Leu Leu Pro Asn Arg
    3005                3010

<210> SEQ ID NO 2
<211> LENGTH: 317
<212> TYPE: DNA
<213> ORGANISM: Mus musculus
<220> FEATURE:
<221> NAME/KEY: CDS
<222> LOCATION: (2)..(316)
<223> OTHER INFORMATION: The 'Xaa' at location 50 stands for Ala, or
      Val. The 'Xaa' at location 60 stands for Gln, or His.
```

<400> SEQUENCE: 2

```
t ttt gag gtg cag ctg gag gag tct ggg gga ggc tta gtg cag cct gga         49
  Phe Glu Val Gln Leu Glu Glu Ser Gly Gly Gly Leu Val Gln Pro Gly
  1               5                   10                  15 ggg tcc cgg aaa ctc tcc tgt gca gcc tct gga ttc act ttc agt agc           97
Gly Ser Arg Lys Leu Ser Cys Ala Ala Ser Gly Phe Thr Phe Ser Ser
            20                  25                  30 ttt gga atg cac tgg gtt cgt cag gct cca gag aag ggg ctg gag tgg          145
Phe Gly Met His Trp Val Arg Gln Ala Pro Glu Lys Gly Leu Glu Trp
        35                  40                  45 gtc gya tac att agt agt ggc agt agt acc ctc cam tat gca gac aca          193
Val Xaa Tyr Ile Ser Ser Gly Ser Ser Thr Leu Xaa Tyr Ala Asp Thr
    50                  55                  60 gtg aag ggc cga ttc acc atc tcc aga gac aat ccc aag aac acc ctg          241
Val Lys Gly Arg Phe Thr Ile Ser Arg Asp Asn Pro Lys Asn Thr Leu
65                  70                  75                  80 ttc ctg caa atg aaa cta ccc tca cta tgc tat gga cta ctg ggg cca          289
Phe Leu Gln Met Lys Leu Pro Ser Leu Cys Tyr Gly Leu Leu Gly Pro
                85                  90                  95 agg gac cac ggt cac cgt ctc ctc aag a                                    317
Arg Asp His Gly His Arg Leu Leu Lys
                100                 105
```

<210> SEQ ID NO 3
<211> LENGTH: 105
<212> TYPE: PRT
<213> ORGANISM: Mus musculus
<220> FEATURE:
<221> NAME/KEY: misc_feature
<222> LOCATION: (50)..(50)
<223> OTHER INFORMATION: The 'Xaa' at location 50 stands for Ala, or Val.
<220> FEATURE:
<221> NAME/KEY: misc_feature
<222> LOCATION: (60)..(60)
<223> OTHER INFORMATION: The 'Xaa' at location 60 stands for Gln, or His.

<400> SEQUENCE: 3

```
Phe Glu Val Gln Leu Glu Glu Ser Gly Gly Gly Leu Val Gln Pro Gly
1               5                   10                  15

Gly Ser Arg Lys Leu Ser Cys Ala Ala Ser Gly Phe Thr Phe Ser Ser
            20                  25                  30

Phe Gly Met His Trp Val Arg Gln Ala Pro Glu Lys Gly Leu Glu Trp
        35                  40                  45

Val Xaa Tyr Ile Ser Ser Gly Ser Ser Thr Leu Xaa Tyr Ala Asp Thr
    50                  55                  60

Val Lys Gly Arg Phe Thr Ile Ser Arg Asp Asn Pro Lys Asn Thr Leu
65                  70                  75                  80

Phe Leu Gln Met Lys Leu Pro Ser Leu Cys Tyr Gly Leu Leu Gly Pro
                85                  90                  95

Arg Asp His Gly His Arg Leu Leu Lys
                100                 105
```

<210> SEQ ID NO 4
<211> LENGTH: 330
<212> TYPE: DNA
<213> ORGANISM: Mus musculus
<220> FEATURE:
<221> NAME/KEY: CDS
<222> LOCATION: (5)..(325)

-continued

<400> SEQUENCE: 4

```
gttt gac att ctg atg acc cag tct cac aaa ttc atg tcc aca tca ata       49
     Asp Ile Leu Met Thr Gln Ser His Lys Phe Met Ser Thr Ser Ile
     1               5                   10                  15 gga gac agg gtc agc gtc acc tgc aag gcc agt cag gat gtg ggt act       97
Gly Asp Arg Val Ser Val Thr Cys Lys Ala Ser Gln Asp Val Gly Thr
                20                  25                  30 gct gta gcc tgg tat caa caa aaa cca ggg caa tct cct aaa ctt ctg      145
Ala Val Ala Trp Tyr Gln Gln Lys Pro Gly Gln Ser Pro Lys Leu Leu
            35                  40                  45 att tac tgg gca tcc acc cgg cac act gga gtc cct gat cgc ttc aca      193
Ile Tyr Trp Ala Ser Thr Arg His Thr Gly Val Pro Asp Arg Phe Thr
        50                  55                  60 ggc agt gga tct ggg aca gat ttc act ctc acc ttt aac aat gtg cag      241
Gly Ser Gly Ser Gly Thr Asp Phe Thr Leu Thr Phe Asn Asn Val Gln
65                  70                  75                  80 tct gaa gac tta gca gat tat ttc tgt cag caa tat agc aac ttt cct      289
Ser Glu Asp Leu Ala Asp Tyr Phe Cys Gln Gln Tyr Ser Asn Phe Pro
                85                  90                  95 ctc acg ttc ggc tcg ggg acc aag ctg gag atc taa caaaa                330
Leu Thr Phe Gly Ser Gly Thr Lys Leu Glu Ile
                100                 105
```

<210> SEQ ID NO 5
<211> LENGTH: 106
<212> TYPE: PRT
<213> ORGANISM: Mus musculus

<400> SEQUENCE: 5

```
Asp Ile Leu Met Thr Gln Ser His Lys Phe Met Ser Thr Ser Ile Gly
1               5                   10                  15

Asp Arg Val Ser Val Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Phe Asn Asn Val Gln Ser
65                  70                  75                  80

Glu Asp Leu Ala Asp Tyr Phe Cys Gln Gln Tyr Ser Asn Phe Pro Leu
                85                  90                  95

Thr Phe Gly Ser Gly Thr Lys Leu Glu Ile
            100                 105
```

<210> SEQ ID NO 6
<211> LENGTH: 347
<212> TYPE: DNA
<213> ORGANISM: Mus musculus
<220> FEATURE:
<221> NAME/KEY: CDS
<222> LOCATION: (2)..(346)

<400> SEQUENCE: 6

```
t ttt gag gtg cag ctg gag gag tcg gga cct ggc ctg gtg aaa cct tct       49
  Phe Glu Val Gln Leu Glu Glu Ser Gly Pro Gly Leu Val Lys Pro Ser
  1               5                   10                  15 cag tct ctg tcc ctc acc tgc act gtc act ggc tac tca atc acc agt       97
Gln Ser Leu Ser Leu Thr Cys Thr Val Thr Gly Tyr Ser Ile Thr Ser
            20                  25                  30 gat tat gcc tgg agc tgg atc cgg cag ttt cca gga aac aaa ctg gag      145
Asp Tyr Ala Trp Ser Trp Ile Arg Gln Phe Pro Gly Asn Lys Leu Glu
```

```
Asp Tyr Ala Trp Ser Trp Ile Arg Gln Phe Pro Gly Asn Lys Leu Glu
            35                  40                  45 tgg atg gcc tac ata ggc tac agt ggt aat act agc tac aac cca tct      193
Trp Met Ala Tyr Ile Gly Tyr Ser Gly Asn Thr Ser Tyr Asn Pro Ser
 50                  55                  60 ctc aaa agt cga ata tct gtc act cga gac aca acc aag aac cag ttc      241
Leu Lys Ser Arg Ile Ser Val Thr Arg Asp Thr Thr Lys Asn Gln Phe
 65                  70                  75                  80 ttc ctg agg ttg aaa tct gtg act act gag gac aca gcc aca tat tac      289
Phe Leu Arg Leu Lys Ser Val Thr Thr Glu Asp Thr Ala Thr Tyr Tyr
                 85                  90                  95 tgt tct gcg gta gat ggt tct tac tgg ggc caa ggg acc acg gtc acc      337
Cys Ser Ala Val Asp Gly Ser Tyr Trp Gly Gln Gly Thr Thr Val Thr
                100                 105                 110 gtc tcc tca a                                                        347
Val Ser Ser
        115

<210> SEQ ID NO 7
<211> LENGTH: 115
<212> TYPE: PRT
<213> ORGANISM: Mus musculus

<400> SEQUENCE: 7

Phe Glu Val Gln Leu Glu Glu Ser Gly Pro Gly Leu Val Lys Pro Ser
 1               5                  10                  15

Gln Ser Leu Ser Leu Thr Cys Thr Val Thr Gly Tyr Ser Ile Thr Ser
                20                  25                  30

Asp Tyr Ala Trp Ser Trp Ile Arg Gln Phe Pro Gly Asn Lys Leu Glu
            35                  40                  45

Trp Met Ala Tyr Ile Gly Tyr Ser Gly Asn Thr Ser Tyr Asn Pro Ser
 50                  55                  60

Leu Lys Ser Arg Ile Ser Val Thr Arg Asp Thr Thr Lys Asn Gln Phe
 65                  70                  75                  80

Phe Leu Arg Leu Lys Ser Val Thr Thr Glu Asp Thr Ala Thr Tyr Tyr
                 85                  90                  95

Cys Ser Ala Val Asp Gly Ser Tyr Trp Gly Gln Gly Thr Thr Val Thr
                100                 105                 110

Val Ser Ser
        115

<210> SEQ ID NO 8
<211> LENGTH: 323
<212> TYPE: DNA
<213> ORGANISM: Mus musculus
<220> FEATURE:
<221> NAME/KEY: CDS
<222> LOCATION: (2)..(322)

<400> SEQUENCE: 8 t gac att ctg atg acc cag tct cac aaa ttc atg tcc aca tca cta gga    49
  Asp Ile Leu Met Thr Gln Ser His Lys Phe Met Ser Thr Ser Leu Gly
   1               5                  10                  15 gac agg gtc tgc atc acc tgc cag gcc agt ctg aat ttg ggt act cct      97
Asp Arg Val Cys Ile Thr Cys Gln Ala Ser Leu Asn Leu Gly Thr Pro
                20                  25                  30 gta gtc tgg ttt caa cag aaa cca ggg caa tct cct aaa ctc ctg att      145
Val Val Trp Phe Gln Gln Lys Pro Gly Gln Ser Pro Lys Leu Leu Ile
            35                  40                  45 tac agg aca gcc acc cgg cac act gga atc cct gat cgc ttc aca ggc      193
```

```
Tyr Arg Thr Ala Thr Arg His Thr Gly Ile Pro Asp Arg Phe Thr Gly
    50              55              60 agt gga tct ggg aca gat ttc act ctc acc att acc aat gtg cag tct      241
Ser Gly Ser Gly Thr Asp Phe Thr Leu Thr Ile Thr Asn Val Gln Ser
65              70              75              80 gaa gac ttg gca gat tat ttc tgt gag aaa gat ggc tac tat cct ctc      289
Glu Asp Leu Ala Asp Tyr Phe Cys Glu Lys Asp Gly Tyr Tyr Pro Leu
                85              90              95 acg ttc ggc tcg ggg acc aag ctg gaa ata aaa a                        323
Thr Phe Gly Ser Gly Thr Lys Leu Glu Ile Lys
            100             105

<210> SEQ ID NO 9
<211> LENGTH: 107
<212> TYPE: PRT
<213> ORGANISM: Mus musculus

<400> SEQUENCE: 9

Asp Ile Leu Met Thr Gln Ser His Lys Phe Met Ser Thr Ser Leu Gly
1               5                   10                  15

Asp Arg Val Cys Ile Thr Cys Gln Ala Ser Leu Asn Leu Gly Thr Pro
            20                  25                  30

Val Val Trp Phe Gln Gln Lys Pro Gly Gln Ser Pro Lys Leu Leu Ile
        35                  40                  45

Tyr Arg Thr Ala Thr Arg His Thr Gly Ile Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Glu Lys Asp Gly Tyr Tyr Pro Leu
                85                  90                  95

Thr Phe Gly Ser Gly Thr Lys Leu Glu Ile Lys
            100                 105
```